(12) United States Patent
Grunhut et al.

(10) Patent No.: US 8,357,125 B2
(45) Date of Patent: Jan. 22, 2013

(54) AUTOINJECTOR WITH DEACTIVATING MEANS MOVEABLE BY A SAFETY SHIELD

(75) Inventors: Guillaume Grunhut, Grenoble (FR); Lionel Maritan, Pierre Chatel (FR)

(73) Assignee: Becton, Dickinson and Company, Franklin Lakes, NJ (US)

( * ) Notice: Subject to any disclaimer, the term of this patent is extended or adjusted under 35 U.S.C. 154(b) by 185 days.

(21) Appl. No.: 12/679,989

(22) PCT Filed: Sep. 25, 2007

(86) PCT No.: PCT/IB2007/004205
§ 371 (c)(1),
(2), (4) Date: Jun. 24, 2010

(87) PCT Pub. No.: WO2009/040607
PCT Pub. Date: Apr. 2, 2009

(65) Prior Publication Data
US 2010/0262083 A1    Oct. 14, 2010

(51) Int. Cl.
*A61M 5/00* (2006.01)
(52) U.S. Cl. ........ 604/240; 604/197; 604/137; 604/229; 604/223; 604/67; 604/82; 604/506; 604/154; 604/198; 604/228; 604/192; 604/110; 604/134; 604/135
(58) Field of Classification Search .................. 604/137, 604/197, 229, 240, 242, 223, 67, 82, 506, 604/154, 198, 228, 192, 110, 134–135
See application file for complete search history.

(56) References Cited

U.S. PATENT DOCUMENTS

| | | | | |
|---|---|---|---|---|
| 8,052,645 | B2 * | 11/2011 | Slate et al. ..................... | 604/154 |
| 2005/0101919 | A1 | 5/2005 | Brunnberg | |
| 2005/0203466 | A1 | 9/2005 | Hommann et al. | |
| 2006/0189938 | A1 | 8/2006 | Hommann et al. | |

FOREIGN PATENT DOCUMENTS

| | | | |
|---|---|---|---|
| JP | 2007132353 A | * | 5/2007 |
| WO | 02/47746 A1 | | 6/2002 |
| WO | 2007/036676 A1 | | 4/2007 |
| WO | WO 2007036676 A1 | * | 4/2007 |
| WO | WO 2007051330 A1 | * | 5/2007 |
| WO | 2007/099044 A1 | | 9/2007 |
| WO | WO 2007099044 A1 | * | 9/2007 |
| WO | 2007/132353 A2 | | 11/2007 |
| WO | WO 2007132353 A2 | * | 11/2007 |

* cited by examiner

*Primary Examiner* — Nicholas Lucchesi
*Assistant Examiner* — Scott Medway
(74) *Attorney, Agent, or Firm* — Hoffmann & Baron, LLP

(57) ABSTRACT

The invention relates to an injection device (1) being in one of a passive and active state, triggering of injection being prevented when said device (1) is in its passive state and permitted when said device (1) is in its active state, having:
- a housing (30, 30a, 30b) receiving a container, the container being in one of a passive state and an active state, movement of the container out of its initial position being prevented when the container is in its passive state, and being permitted when the container is in its active state, and
- a safety shield (40) coupled with the housing (30) and being movable with respect to the housing along a movement path having a predetermined length,
- first retaining means (60, 61, 54a) for maintaining the container (20) in its passive state,
- second retaining means (34a, 81b) for maintaining said device (1) in its passive state,
- said device (1) being characterized in that it comprises:
- first deactivating means (50, 53) and second deactivating means (50, 50a) movable coincident with movement of the safety shield (40) so as to place the container (20) in the active state, and the device (1) in its active state.

17 Claims, 18 Drawing Sheets

Figure 1:
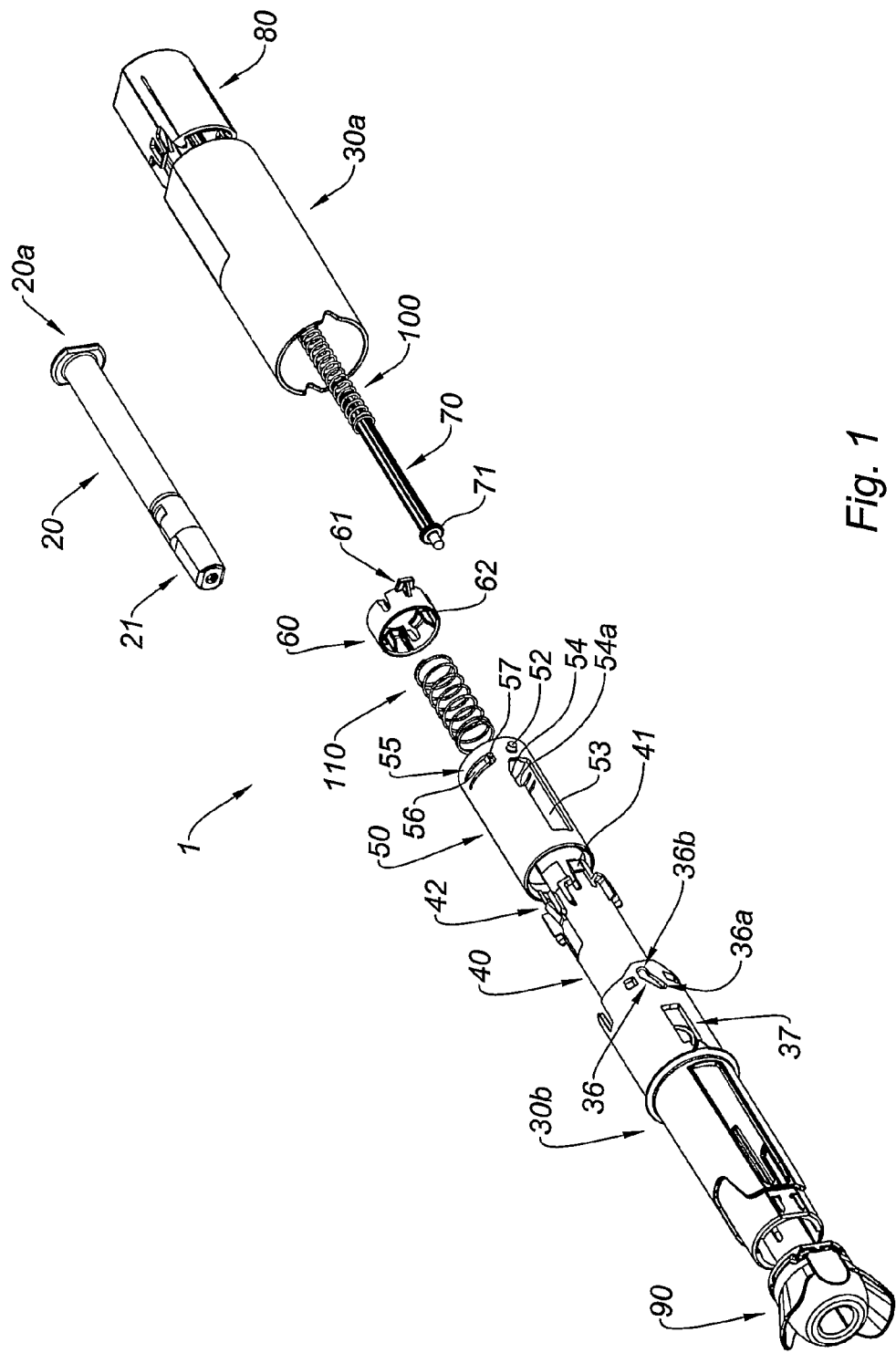

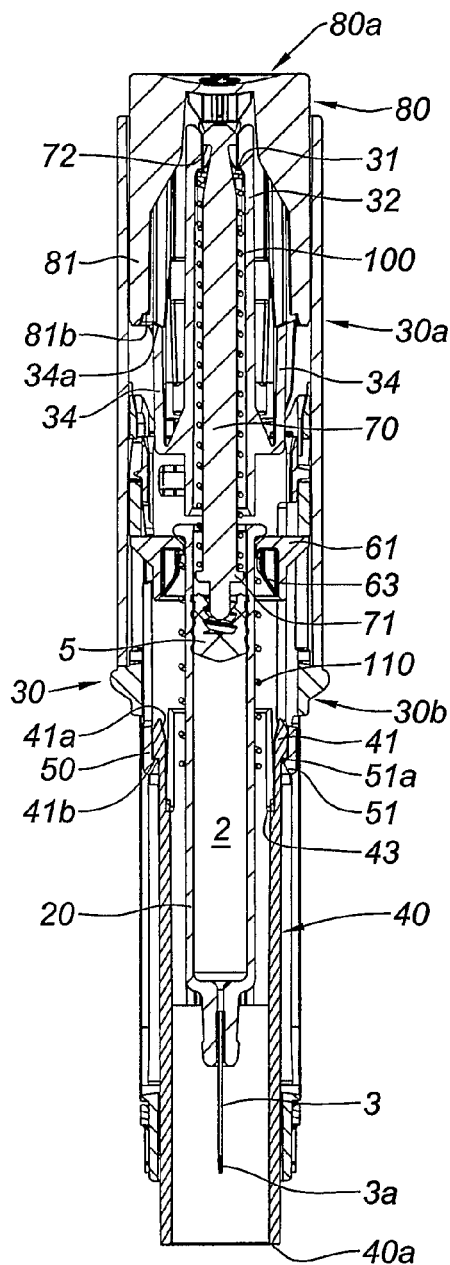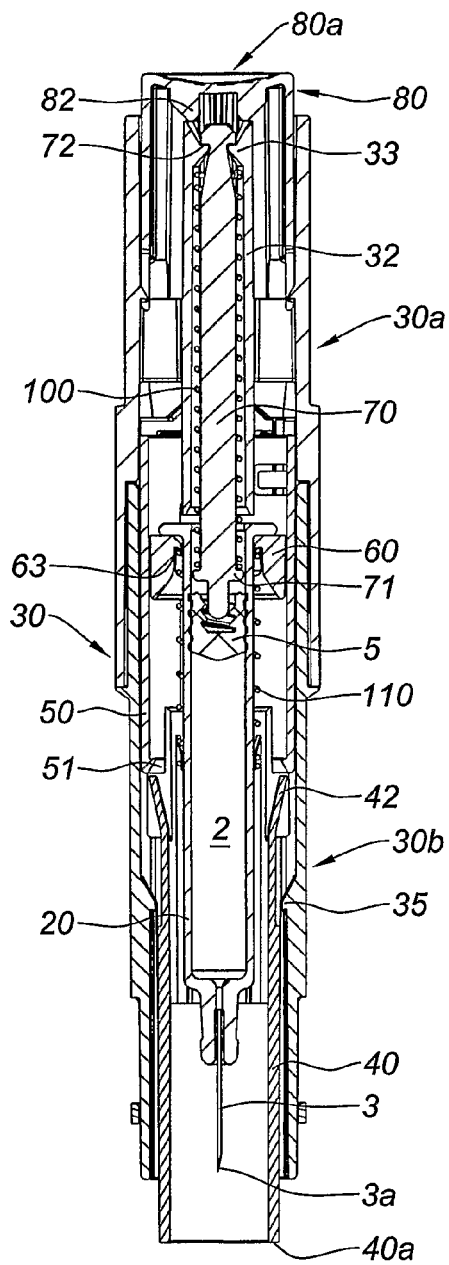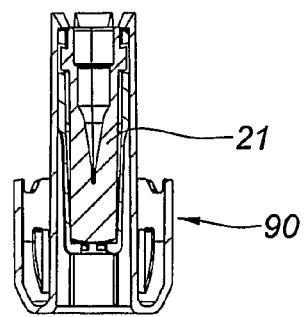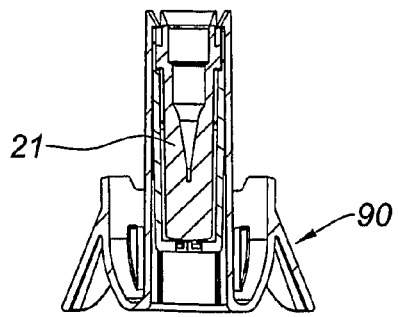
Fig. 7    Fig. 8

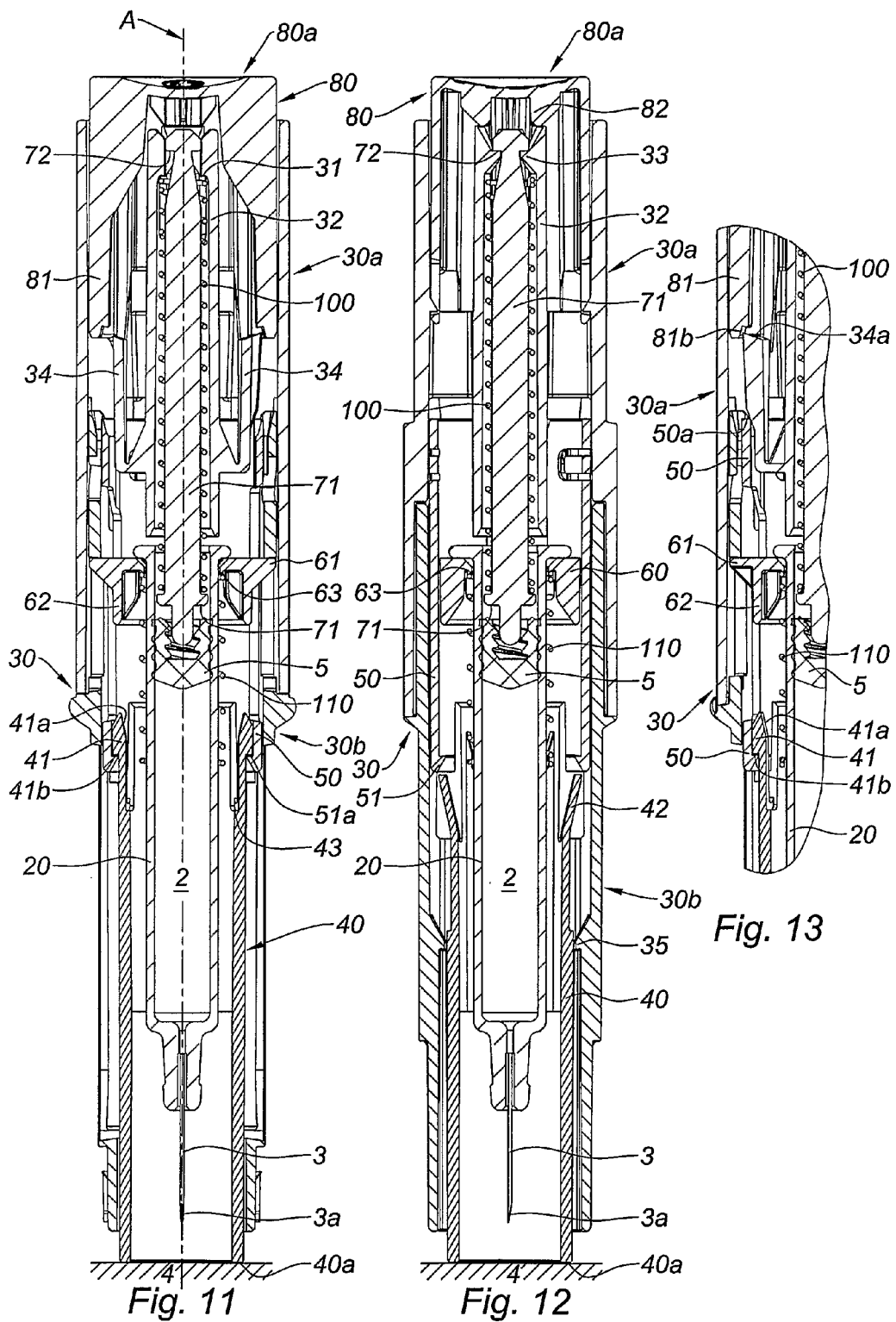

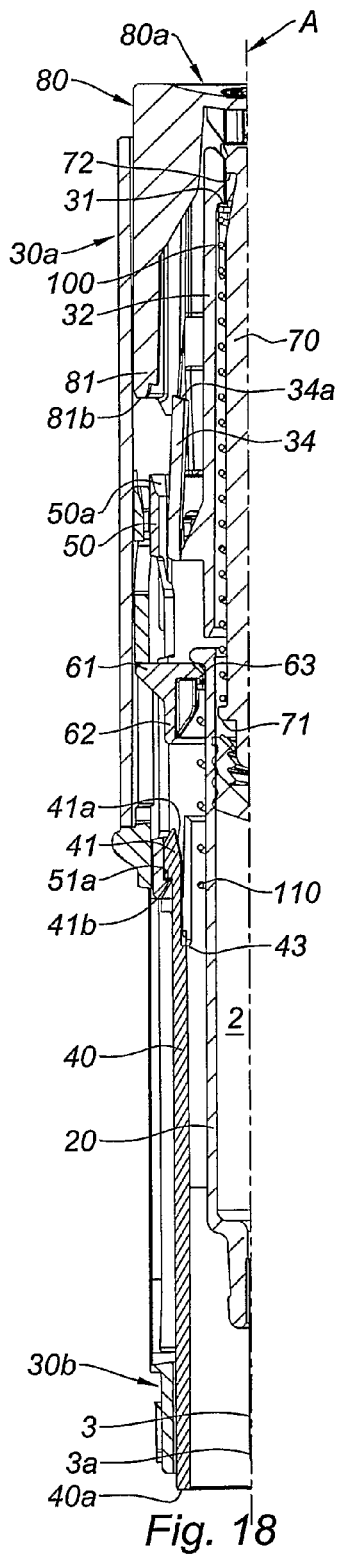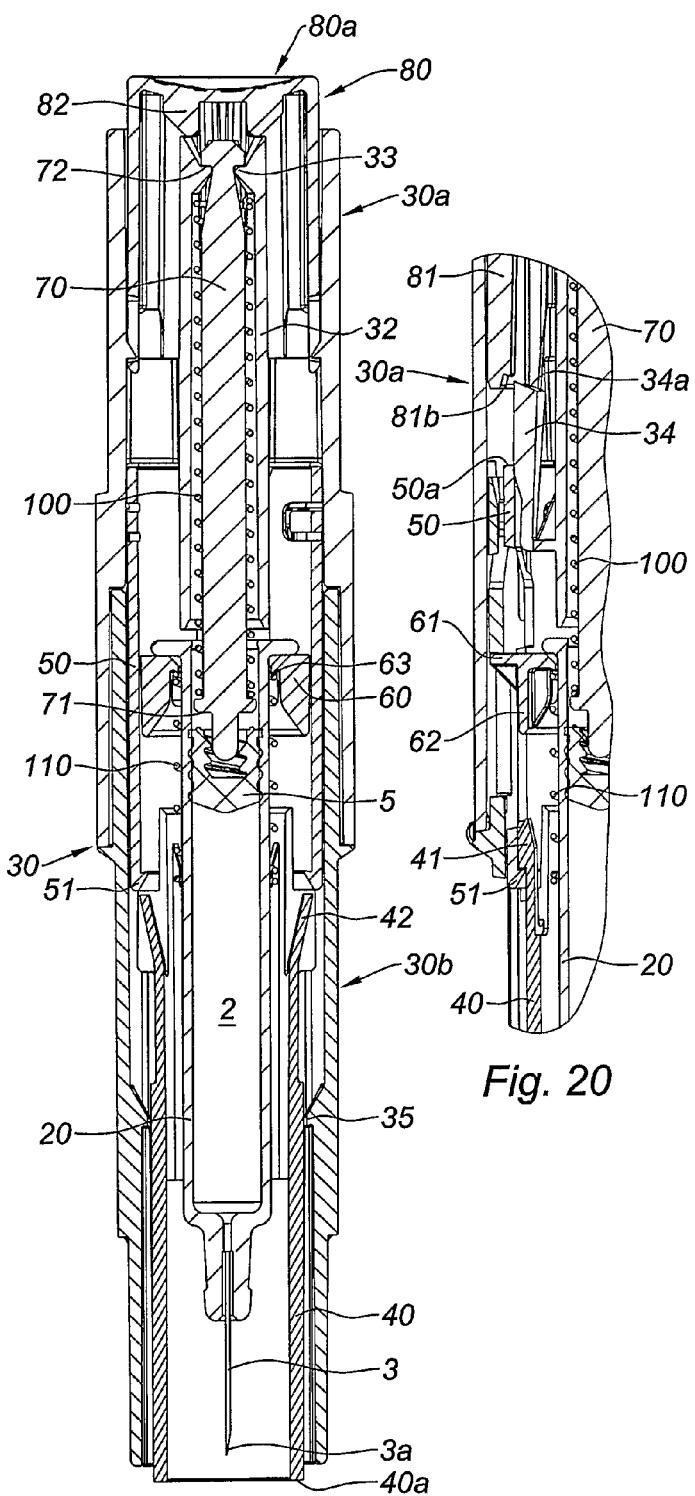
Fig. 18   Fig. 19   Fig. 20

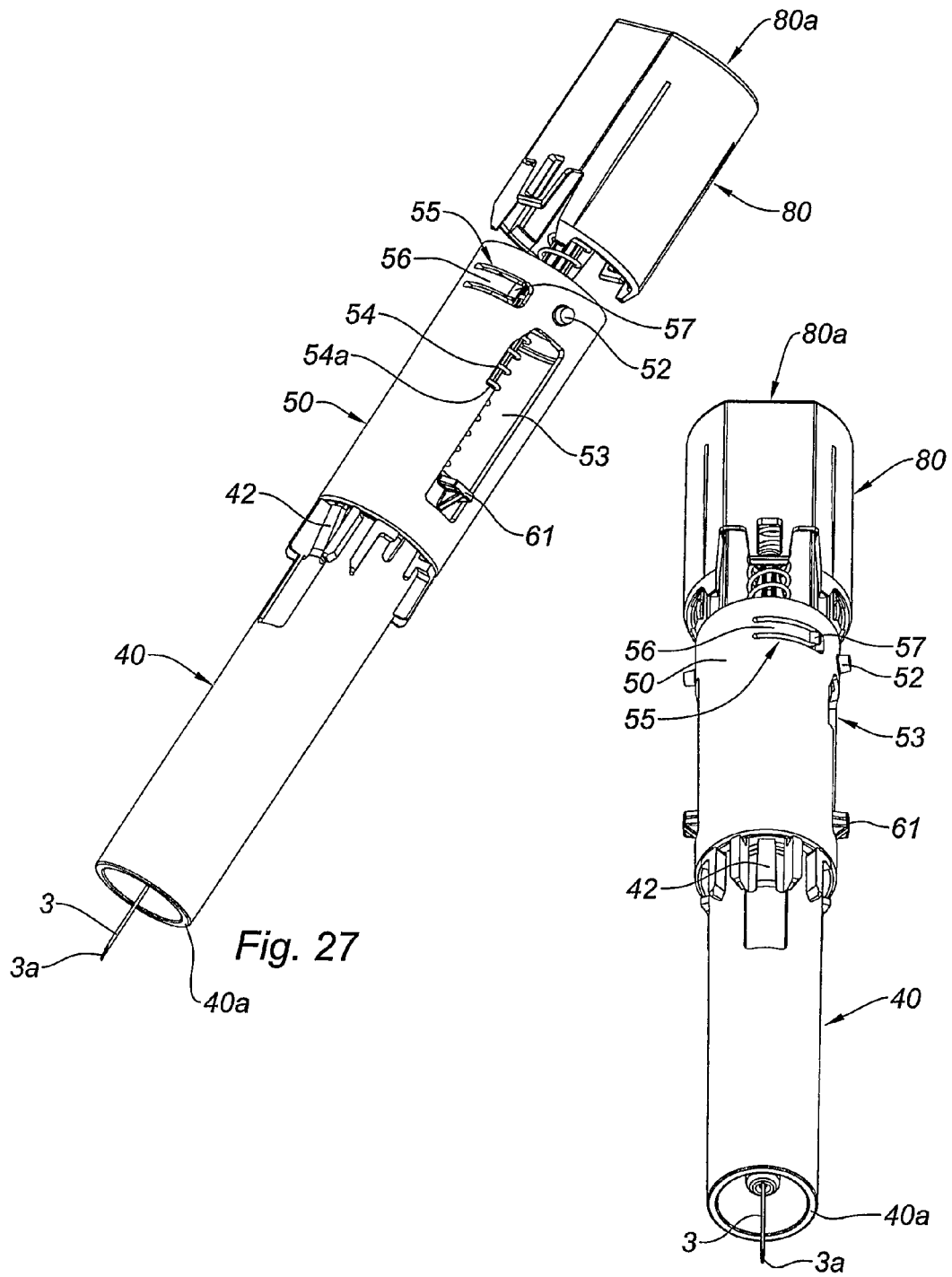

AUTOINJECTOR WITH DEACTIVATING MEANS MOVEABLE BY A SAFETY SHIELD

The present invention relates to a device for automatic injection of a product in a very safe way, especially for self-injection.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, and the "proximal direction" is to be understood as meaning the opposite direction to the direction of injection.

Some illnesses necessitate regular injections of drugs or products, for instance on a daily basis. In order to simplify the treatment, some self-injectors have been provided in order to allow the patient to perform the injection on its own.

Of course, since the patient is usually neither a nurse nor an educated person in medical devices, such self-injectors must prove to be very simple to use and also very safe. In particular, the insertion of the needle must be performed at the right depth, the correct dose of product must be injected, that is to say a complete injection must be performed, and the injector must be deactivated after use before it is disposed of. Preferably, the needle should not be exposed, before and after use, in order to prevent any accidental needlestick injury.

An important requirement of these self-injection devices is that they must not be able to be activated inadvertently, before the patient is ready to perform the injection, and in particular before the device is correctly applied at the right injection site.

Injections devices provided with safety systems preventing the triggering of the insertion of the needle as long as the device is not correctly positioned on the patient's skin have been described.

In some cases though, because the operation of self-injecting a product may be stressful for the user and also because it requires that a high force be applied on the skin at the injection site, the user may, inadvertently or not, displace the self-injection device on the skin, after having triggered the insertion of the needle but before the injection has started. If the injection device is provided with a safety system that covers the needle on displacement or removal of the injection device, the injection device is not usable anymore and the medicinal product is lost.

There is therefore a need for an injection device, in particular for automatic injection, that would reduce the force with which the injection device is to be applied on the skin and that would minimize the risks related to a misuse of the injection device by a non educated person in medical devices.

The present invention meets this need by proposing a device for automatic injection of a product into an injection site, said device comprising a safety system that allows a safe and efficient injection, even if the user moves and/or removes the device from the skin once he has triggered the insertion of the needle.

The present invention relates to a device for automatic injection of a product into an injection site, said device being in one of a passive and active state, triggering of injection being prevented when said device is in its passive state and permitted when said device is in its active state, said device having:

a housing capable of receiving a container, the container being movable relative to the housing between an initial position and an insertion position distally spaced from the initial position, the container being in one of a passive state and an active state, movement of the container out of its initial position being prevented when the container is in its passive state, and being permitted when the container is in its active state, and a safety shield coupled with the housing and being movable with respect to the housing along a movement path having a predetermined length, the safety shield being movable between a first position and a second position a first distance that is less than the predetermined length, and between the second position and a third position a second distance that is less than the predetermined length, first retaining means for maintaining the container in its passive state, second retaining means for maintaining said device in its passive state, said device being characterized in that it further comprises:

first deactivating means movable coincident with movement of the safety shield the first distance to cooperate with first retaining means so as to place the container in the active state, and second deactivating means movable coincident with movement of the safety shield the second distance to cooperate with second retaining means so as to place the device in its active state.

The device of the invention is very simple to use. Moreover, as will appear more clearly from the description below, the device of the invention allows a complete and safe injection even if the user mis uses the device and performs mistakes during the use of the device. In particular, in case the user mis-uses the device of the invention, then the product is not lost and the injection may be correctly and safely completed in the end.

In an embodiment of the invention, part of the first and second deactivating means are formed on a sleeve coupled to the safety shield and being received within said housing, the sleeve being movable in rotation and in translation with respect to the housing when the safety shield moves from its first position to its second position, the sleeve being movable in translation with respect to the housing when the safety shield moves from its second position to its third position.

In an embodiment of the invention, said first retaining means comprises a ring coupled with the housing, the ring comprising at least one outer radial stop, the first deactivating means comprises a window defined in the sleeve and having an abutment surface, the outer radial stop being engageable with the abutment surface when the safety shield is in its first position, and being disengageable from the abutment surface when the safety shield is moved from its first position to its second position.

In an embodiment of the invention:

the second retaining means comprises a radially deflectable leg coupled to the housing, the second deactivating means comprises a projection, defined at a proximal end of said sleeve, the projection being capable of deflecting the radially deflectable leg from a rest position, in which the radially deflectable leg maintains the device in its passive state, to a deflected position, in which the device is in its active state, deflection of the radially deflectable leg from its rest position to its deflected position being caused by movement of the safety shield from its second position to its third position.

In an embodiment of the invention, the device further comprises first guiding means for causing the translational and rotational movement of the sleeve when the safety shield is moved from its first position to its second position, and second guiding means for causing the translational movement of the sleeve with respect to the housing when the safety shield is moved from its second position to its third position, the second guiding means preventing the rotation of he sleeve with respect to the housing as the safety shield is moved to its third position.

In an embodiment of the invention, the first guiding means defines the first distance, and wherein the second guiding means defines the second distance.

In an embodiment of the invention, said first guiding means includes a peg located on the sleeve or on the housing and a first portion of a cam located respectively on the housing or on the sleeve and in which the peg is engaged so as to be able to move slidingly within the cam, the first portion of the cam being inclined with respect to the longitudinal axis of the device, movement of the peg within the first portion of the cam causing translational and rotational movement of the sleeve when the safety shield is moved from its first position to its second position.

In an embodiment of the invention, the second guiding means include a second portion of the cam, the second portion being longitudinal, the junction of the first and said second portions of the cam forming an elbow, the movement of the peg within the second portion of the cam causing translational movement of the sleeve when the safety shield is moved from its second position to its third position.

In an embodiment of the invention, the device further comprises:

first biasing means coupled to the housing for biasing the container toward the insertion position, the first biasing means being in one of a compressed condition, in which the container is in its initial position, and an extended condition, in which the container is in its insertion position, and third retaining means for maintaining the first biasing means in its compressed condition, triggering means being user activatable for releasing the third retaining means, once the device is in its active state.

In an embodiment of the invention, the device comprises return means for biasing the safety shield from its third position to its second position after activation of the triggering means but before the container reaches its insertion position, the second guiding means causing the sleeve to move translationally in the distal direction with respect to the housing until the peg comes in abutment with the elbow formed at the junction between the first portion and second portion of the cam.

In an embodiment of the invention, said return means comprise a spring in a compressed condition when the safety shield is in its third position.

In an embodiment of the invention, the device further comprises locking means for preventing the sleeve to rotate back with respect to the housing under the effect of said return means, the locking means comprising a rotational stop located on the sleeve or on the housing, the rotational stop being engaged in abutment against a longitudinal ridge located on the housing or respectively on the sleeve, thereby preventing the rotation of the sleeve with respect to the housing.

In an embodiment of the invention:

the safety shield being movable with respect to the container from its third position, in which the tip of the needle does not extend beyond a distal end of the safety shield, to a fourth position, in which the tip of the needle extends beyond a distal end of the safety shield, and to a fifth position, in which the tip of the needle does not extend beyond a distal end of the safety shield, movement of said safety shield from its fourth position to its fifth position being caused by release of a distal pressure exerted on said housing, said device further comprises arresting means for maintaining the safety shield in its third position, in which the release of the distal pressure exerted on said housing does not cause the safety shield to move to its fifth position, third deactivating means designed for deactivating the arresting means when the safety shield is in its fourth position second biasing means coupled to the safety shield for biasing the safety shield from its fourth position to its fifth position when distal pressure exerted on the housing is released.

In an embodiment of the invention, the arresting means comprises a flexible leg located on the safety shield, the flexible leg being engaged on an abutment surface located on the sleeve so as to maintain the sleeve coupled to the safety shield when the safety shield is in its third position.

In an embodiment of the invention, the ring being coupled to the container, the third deactivating means comprises a distal skirt located on the ring, the distal skirt cooperating with the flexible leg located on the safety shield so as to deflect the flexible leg, when the container moves from its initial position to its insertion position, thereby causing the safety shield to be in its fourth position.

Figure 2:
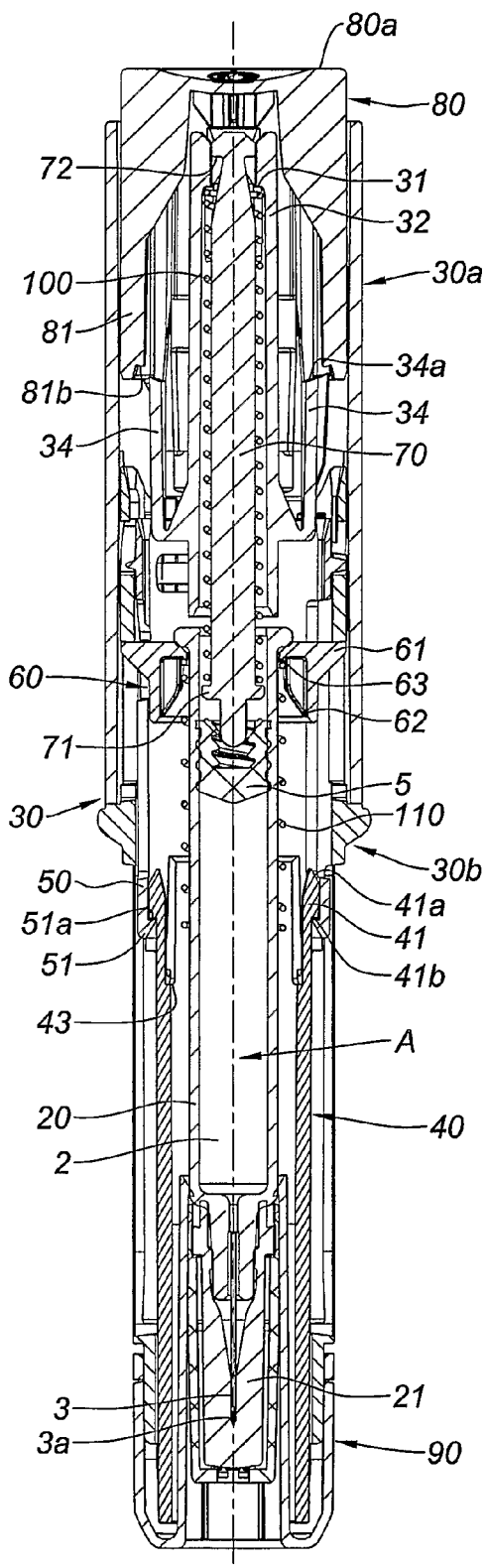
Figure 3:
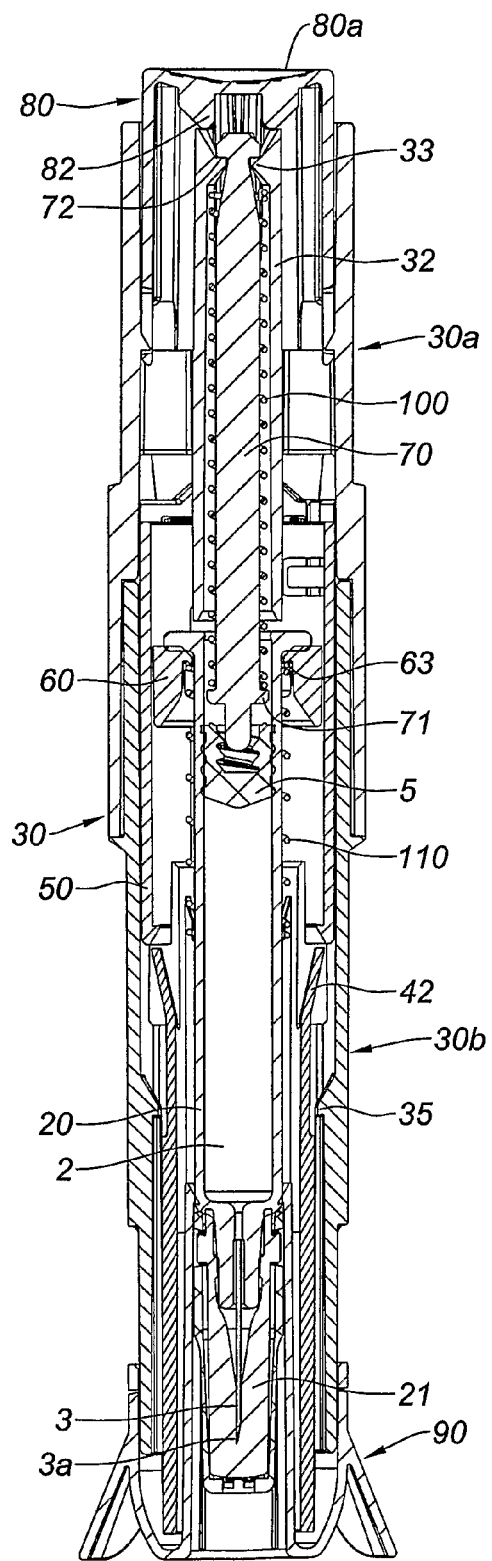
Figures 4, 5:
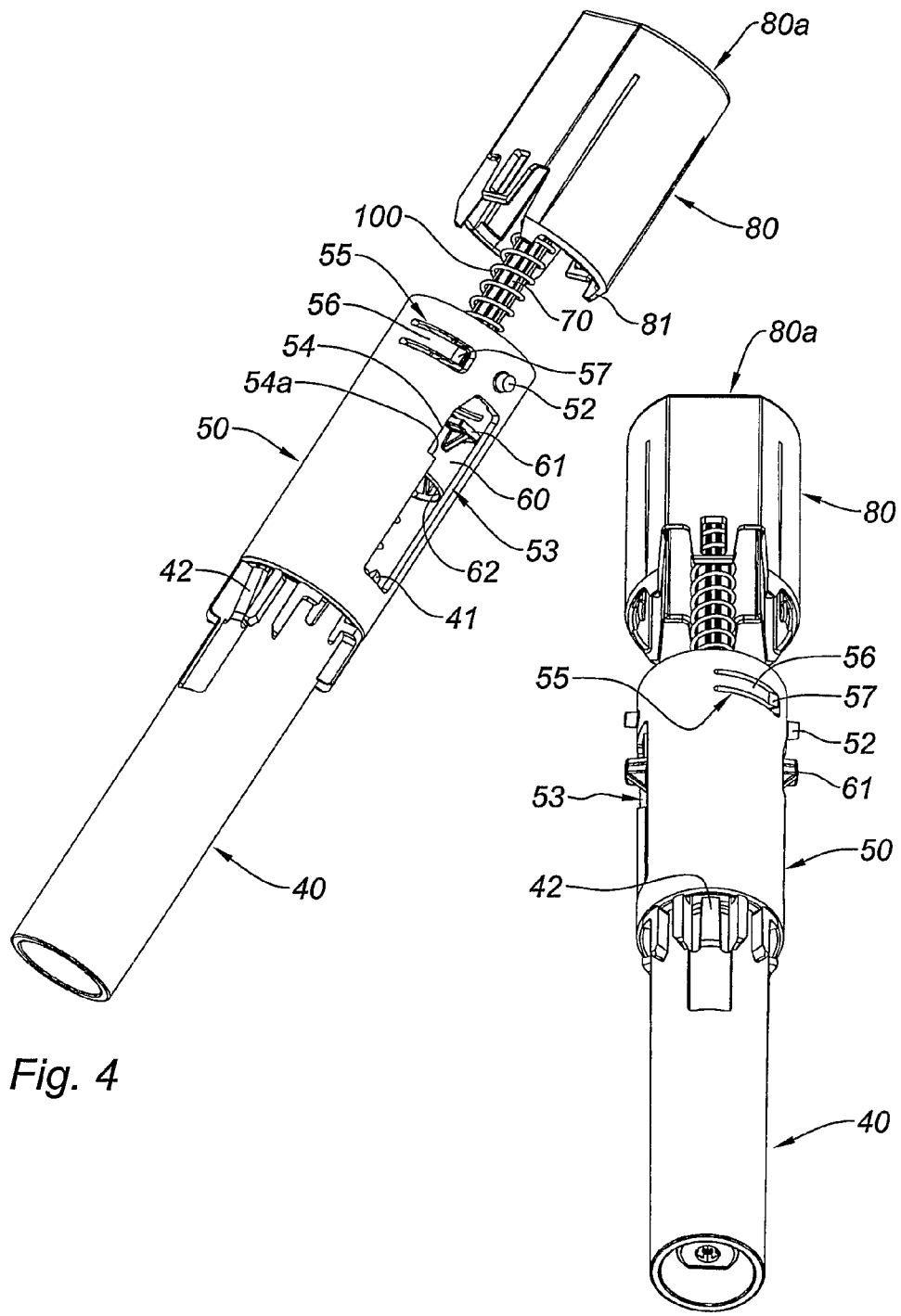
Figure 6:
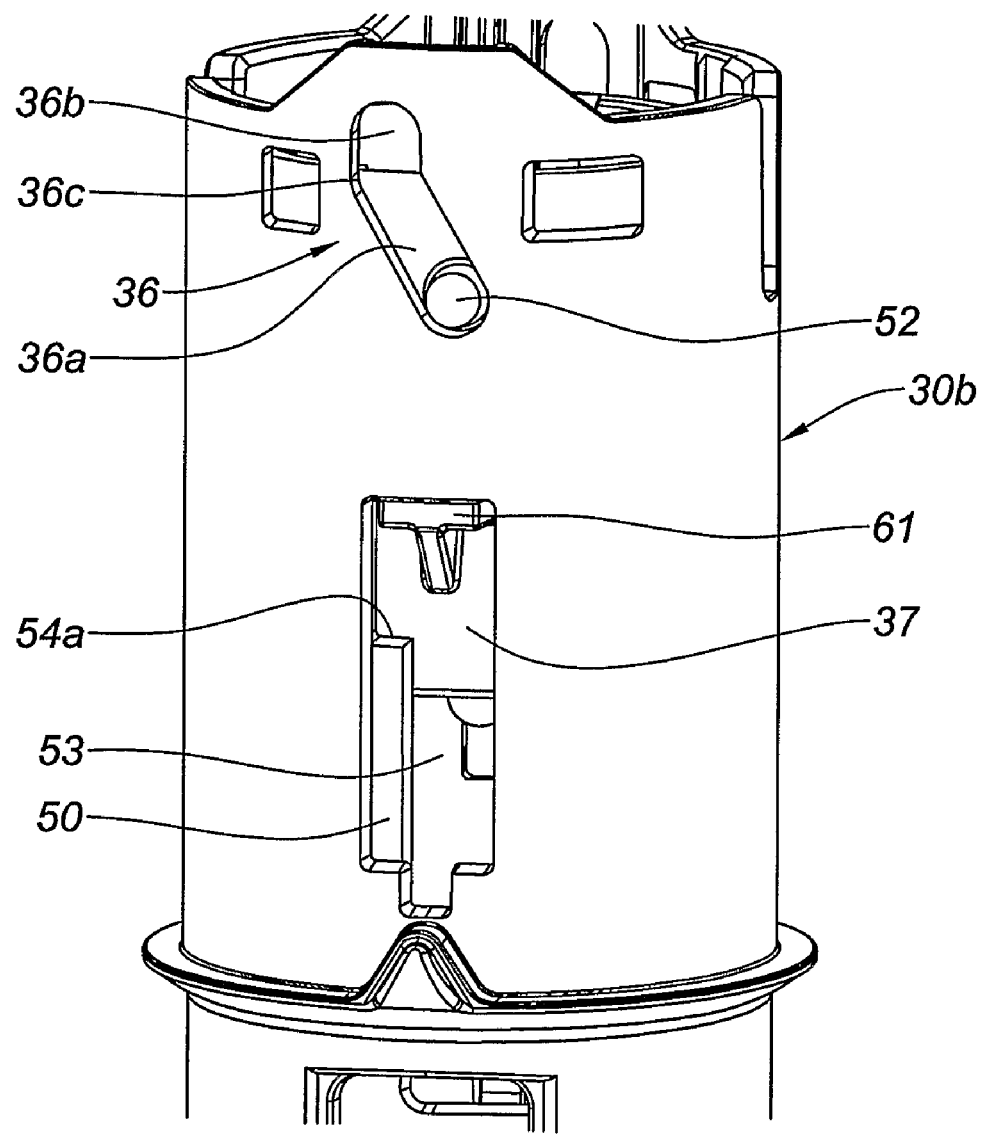
Figure 9:
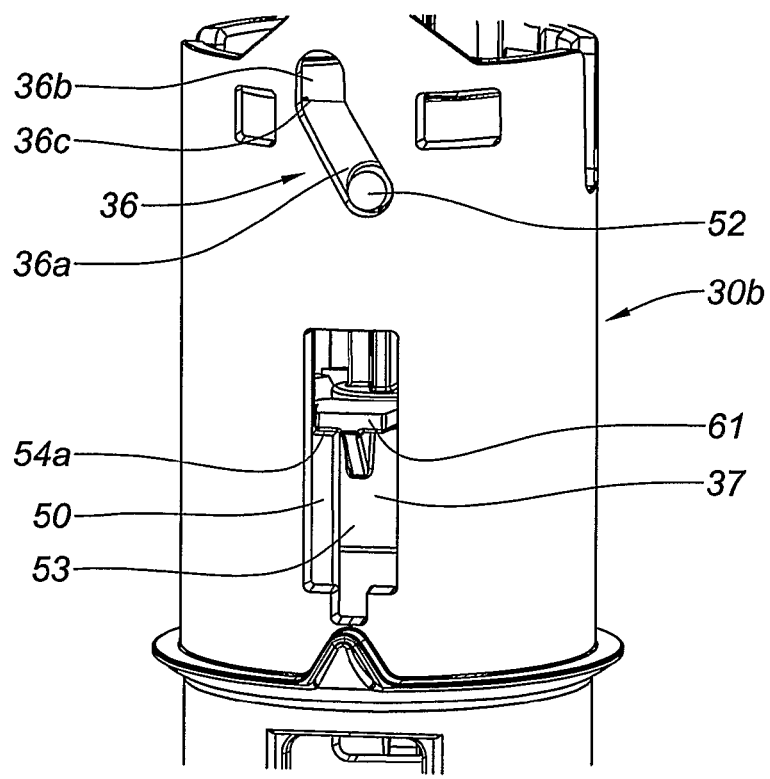
Figure 10:
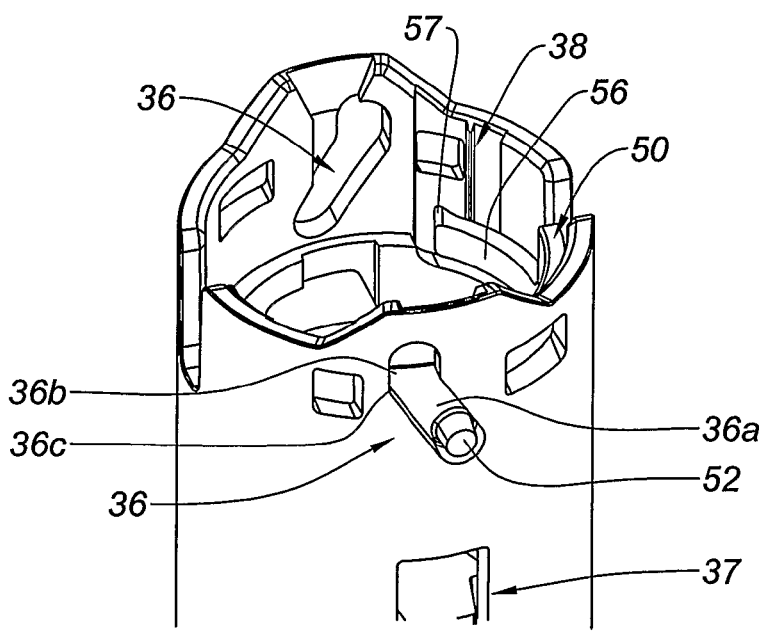
Figure 14:
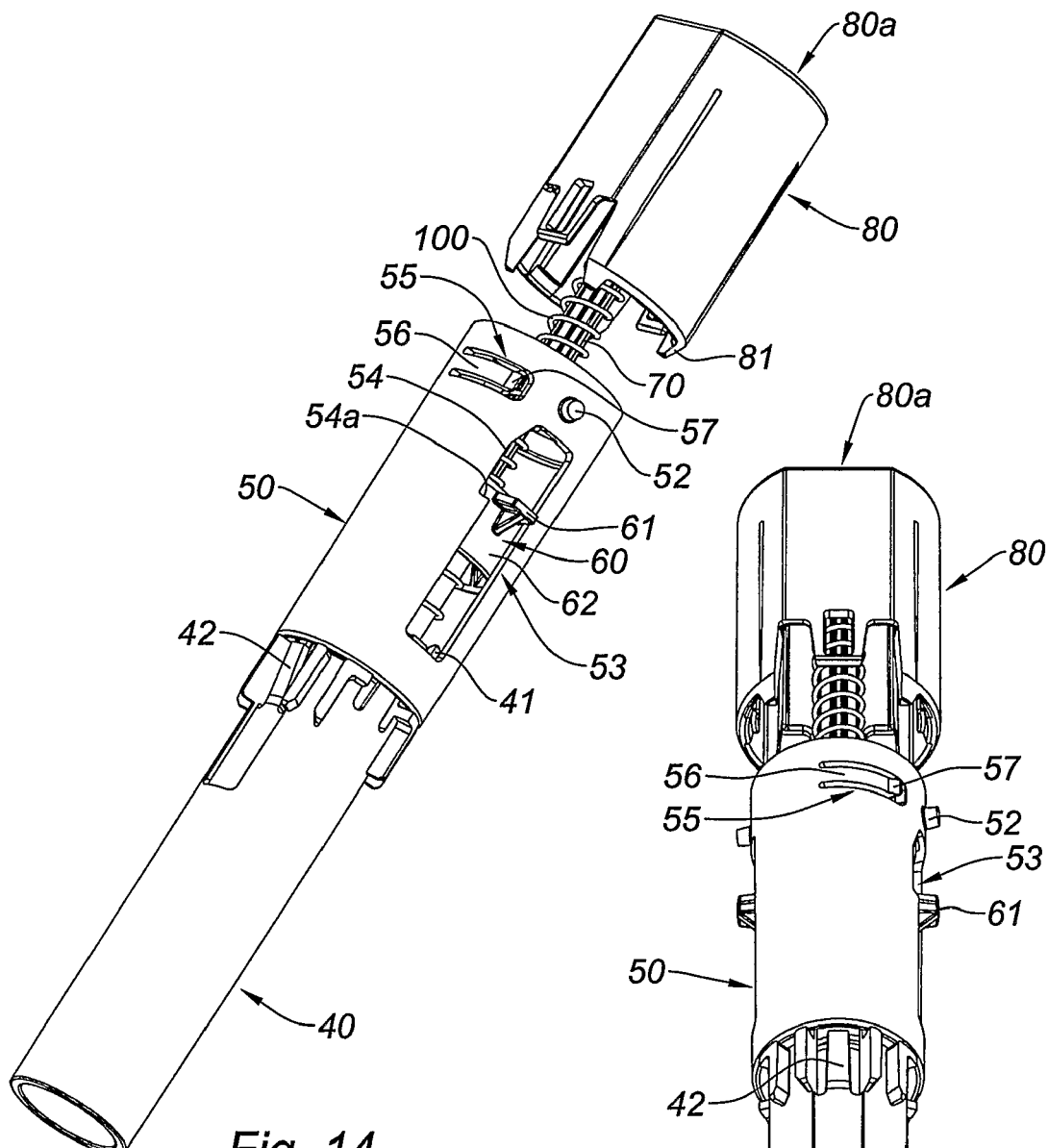
Figure 15:
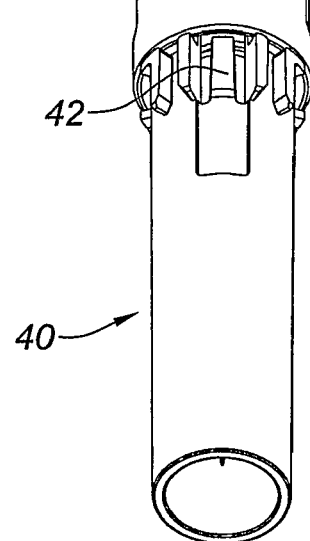
Figure 16:
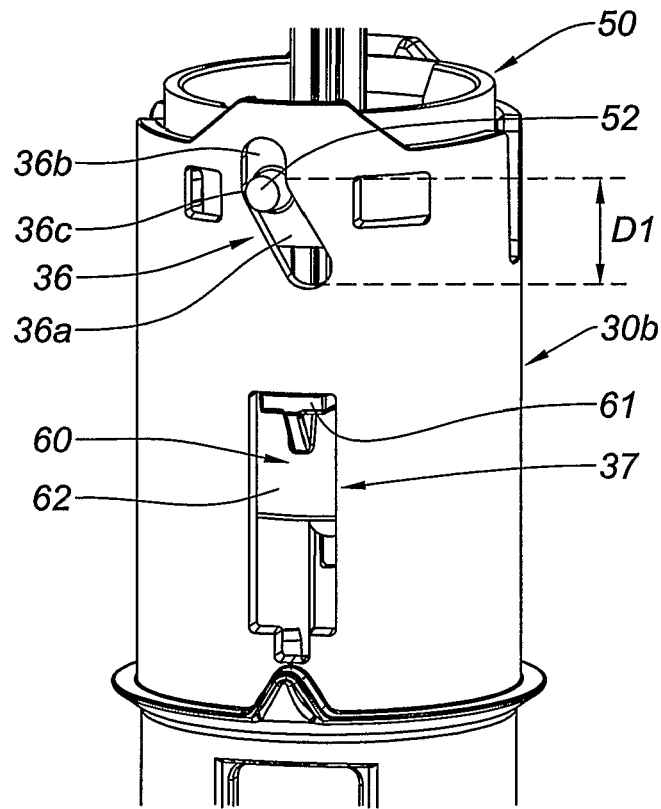
Figure 17:
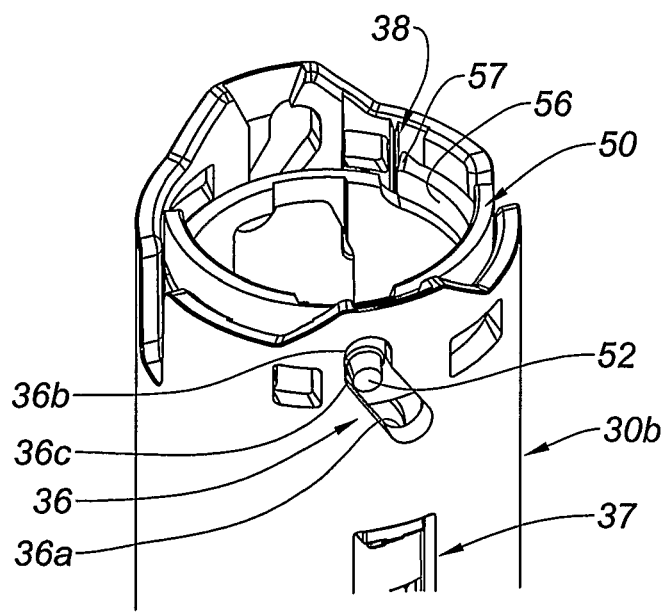
Figures 21, 22:
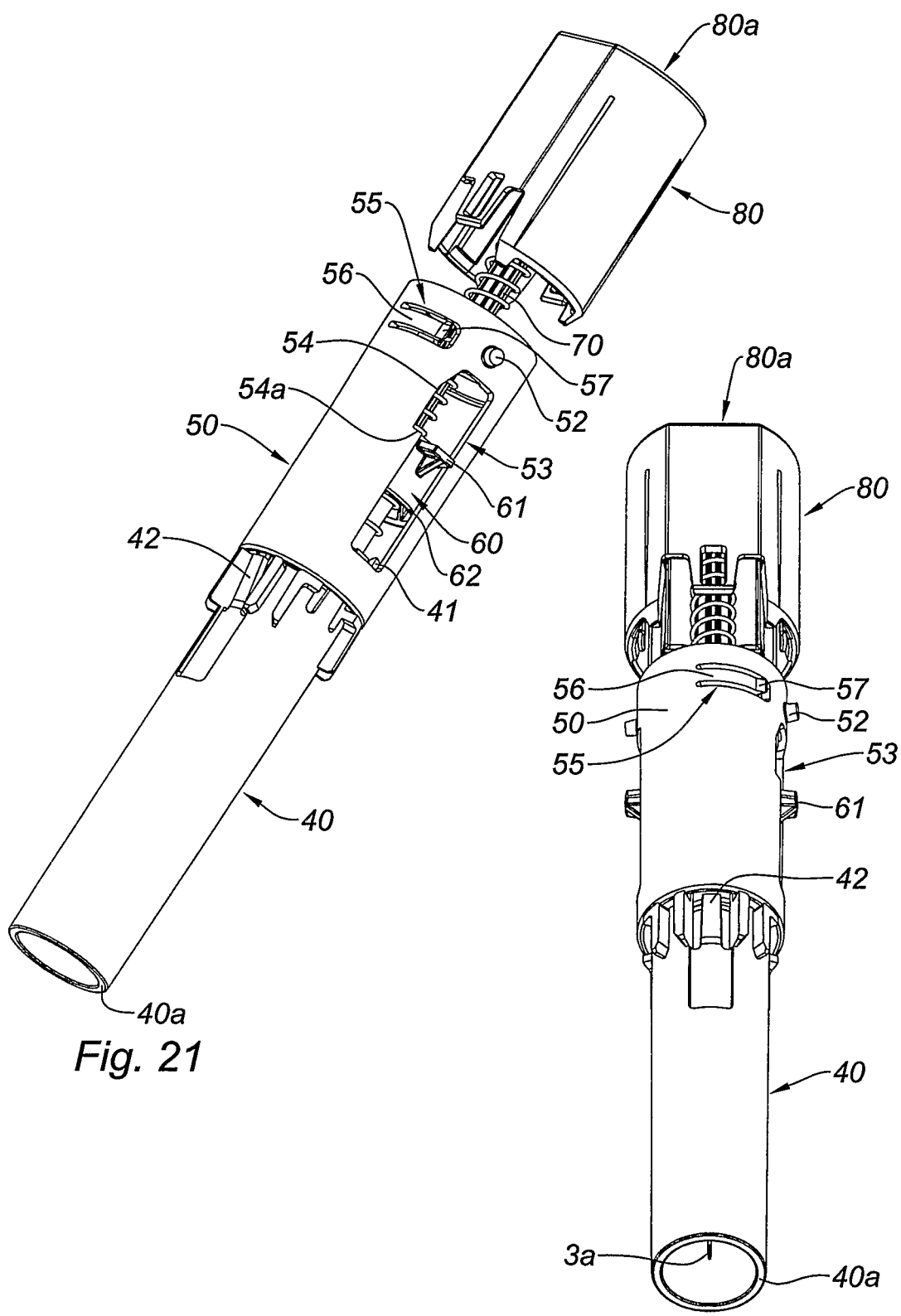
Figure 23:
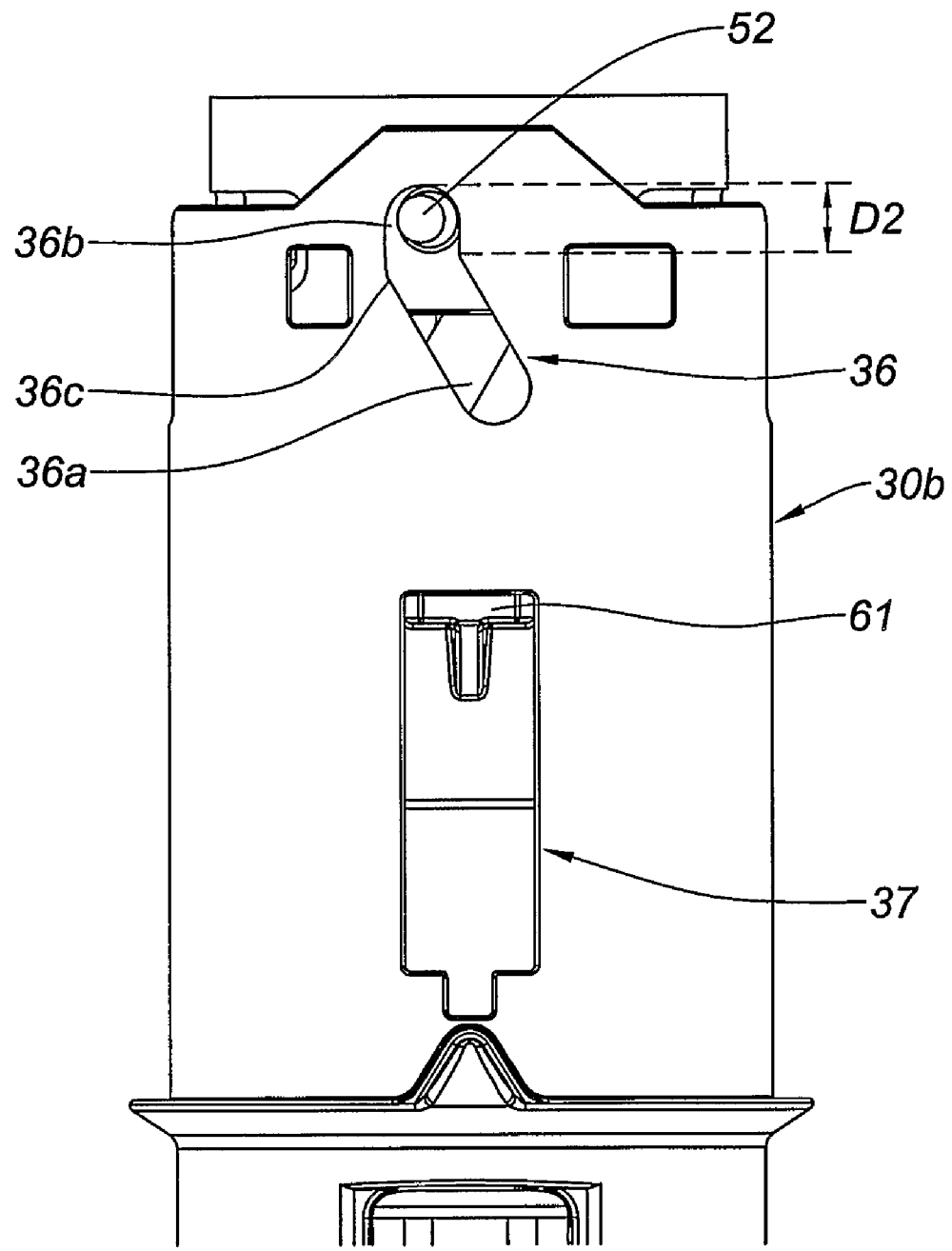
Figure 24:
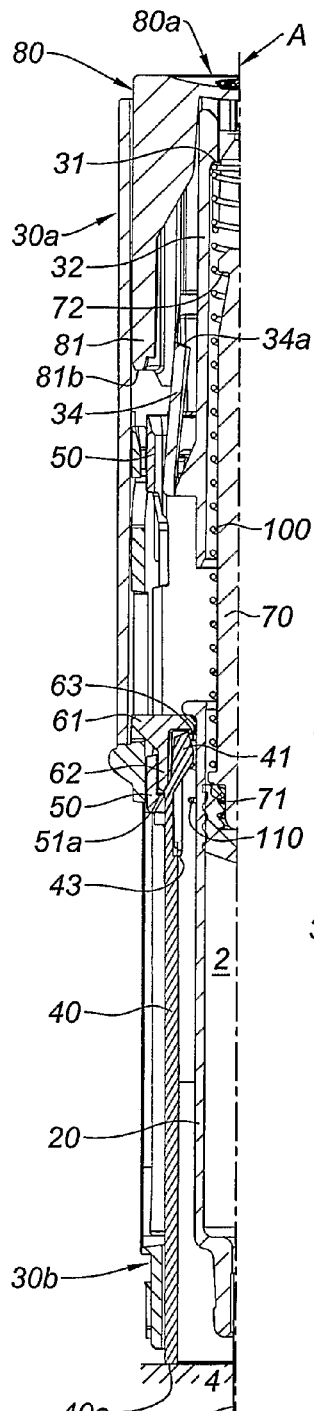
Figure 25:
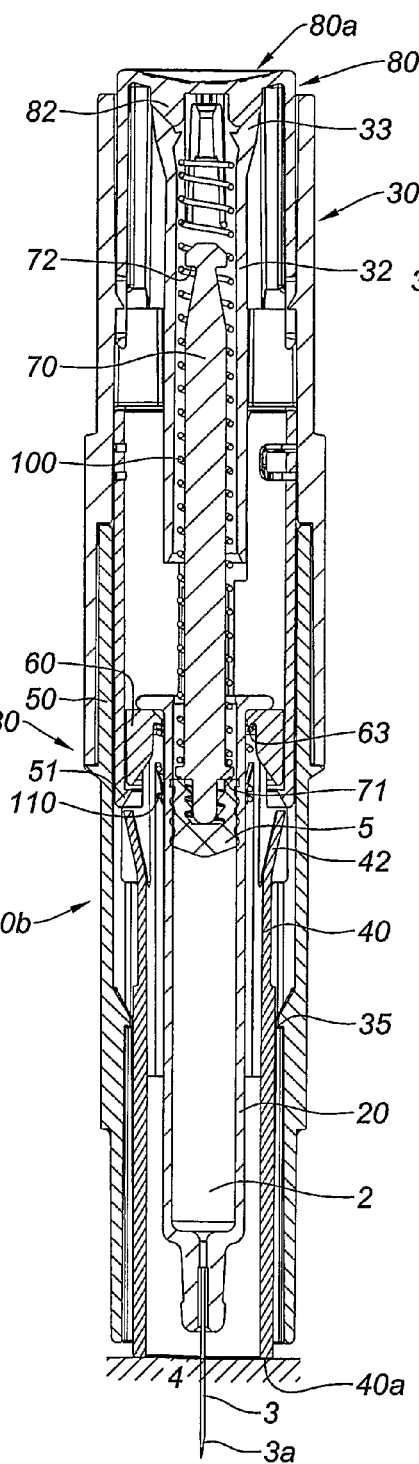
Figure 26:
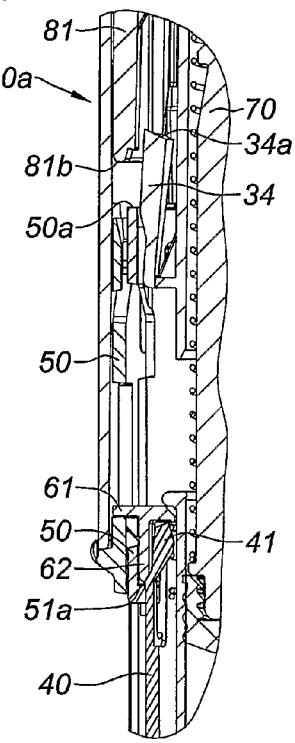
Figures 29, 30, 31:
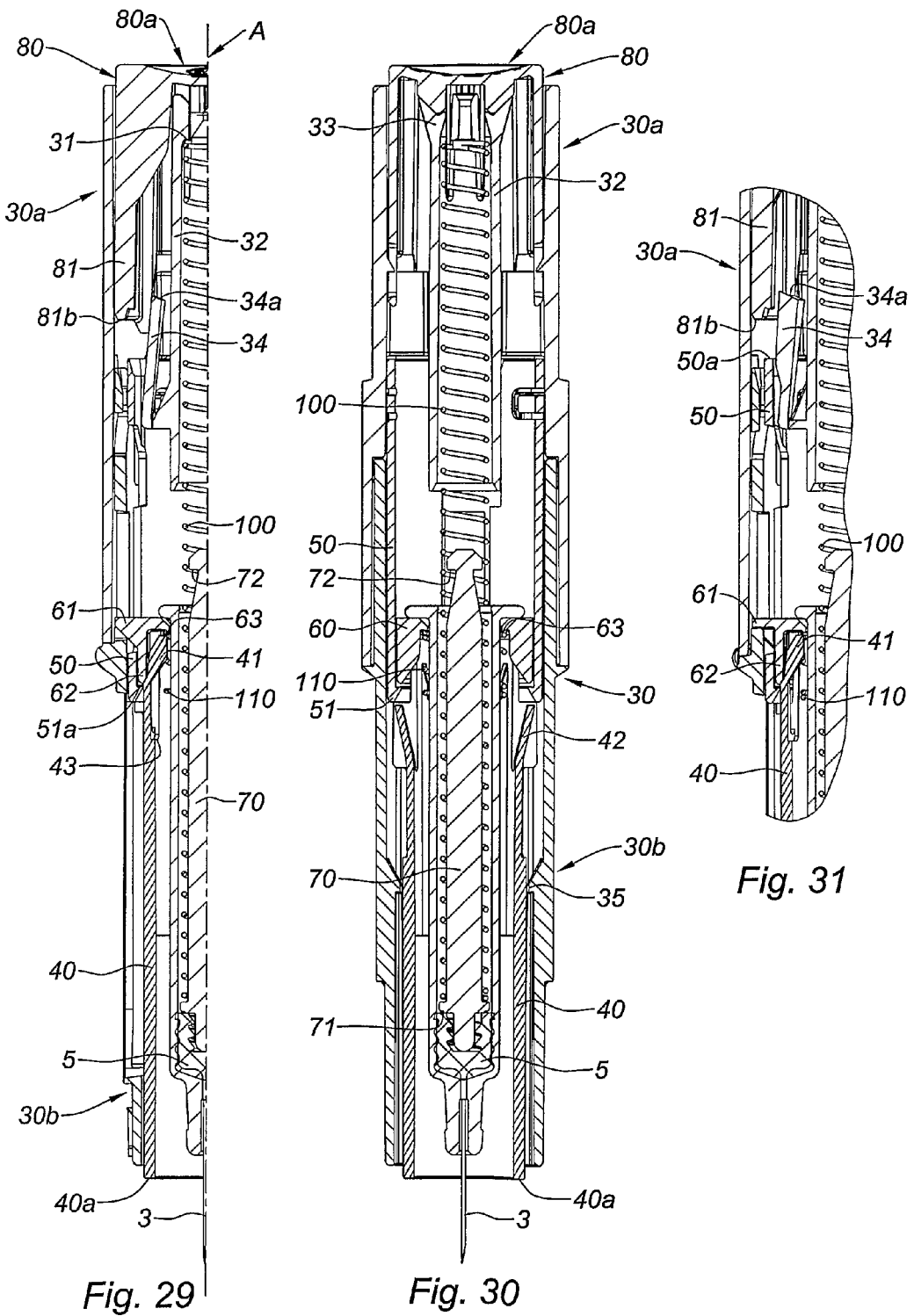
Figure 32:
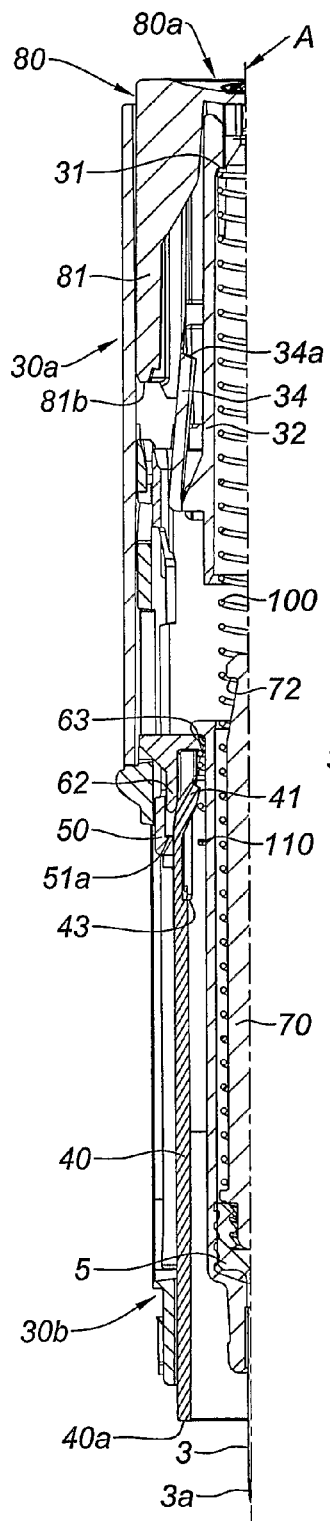
Figure 33:
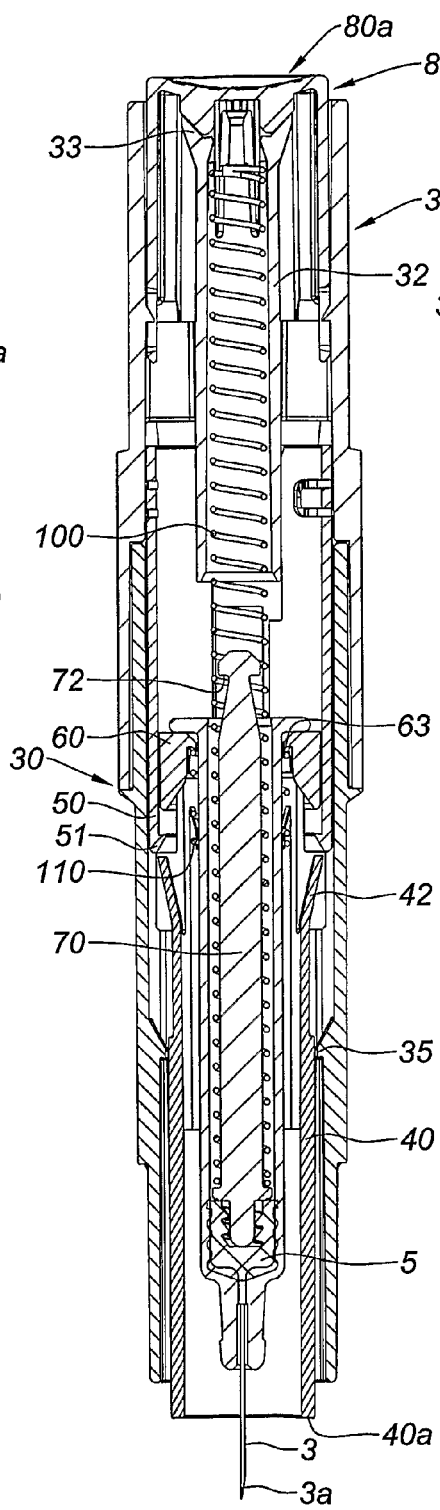
Figure 34:
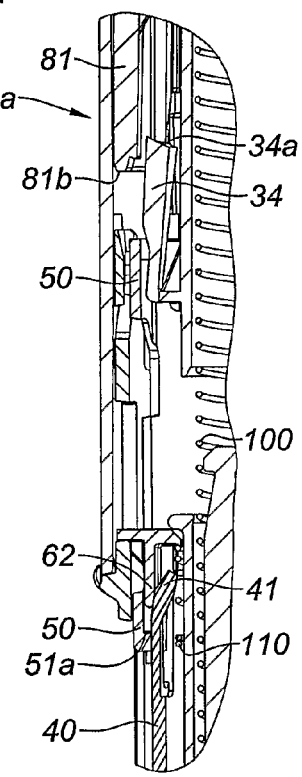
Figure 35:
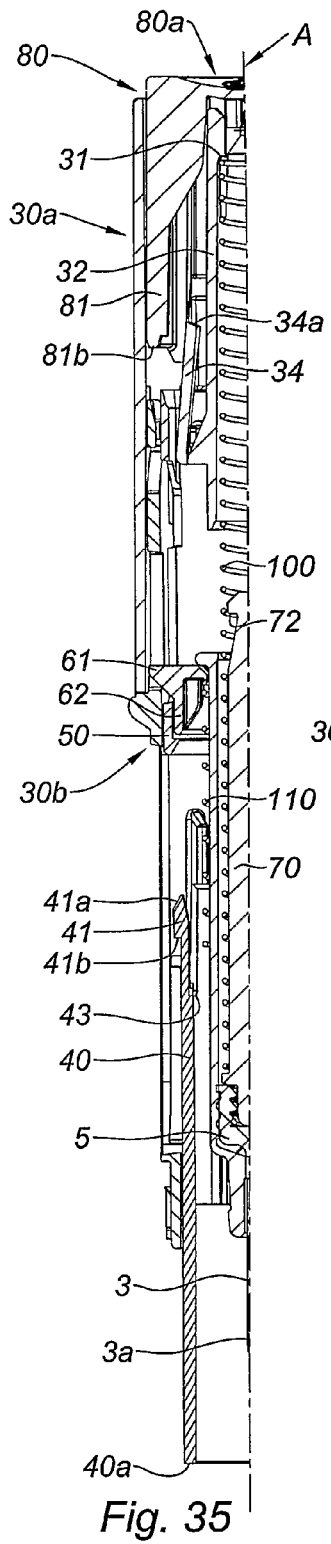
Figure 36:
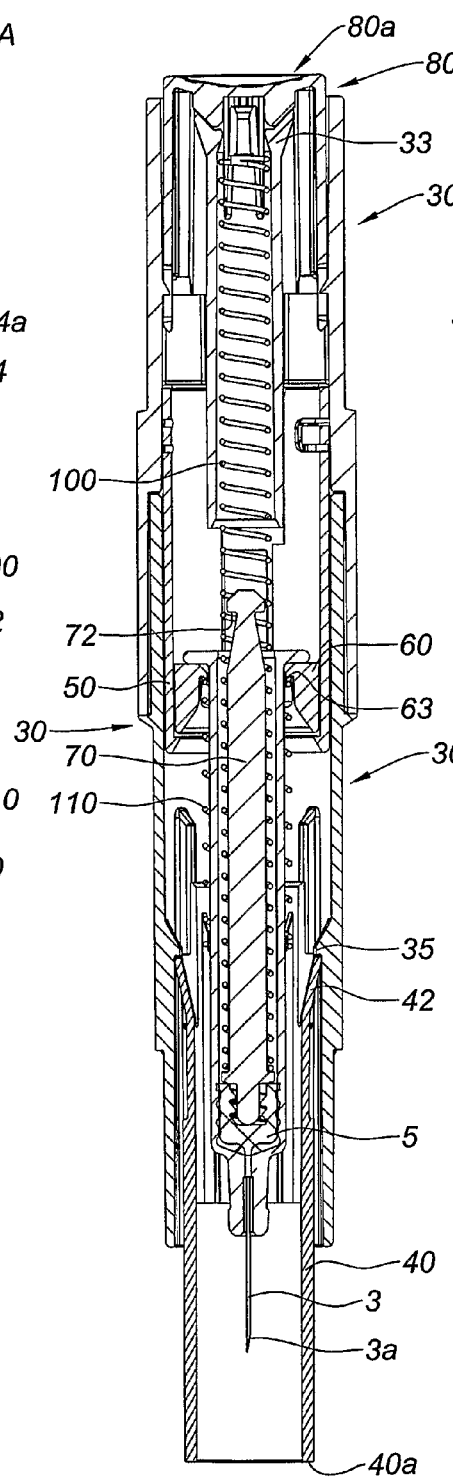
Figure 37:
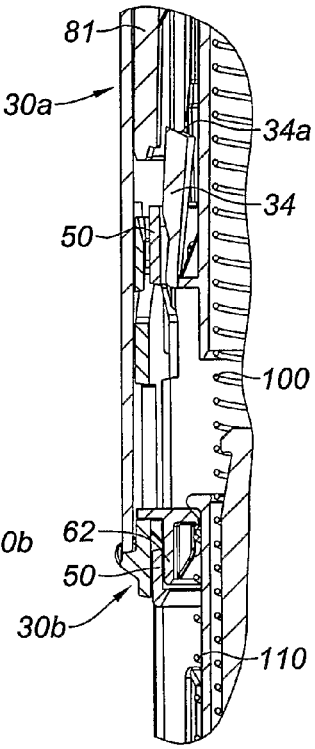
Figures 38, 39:
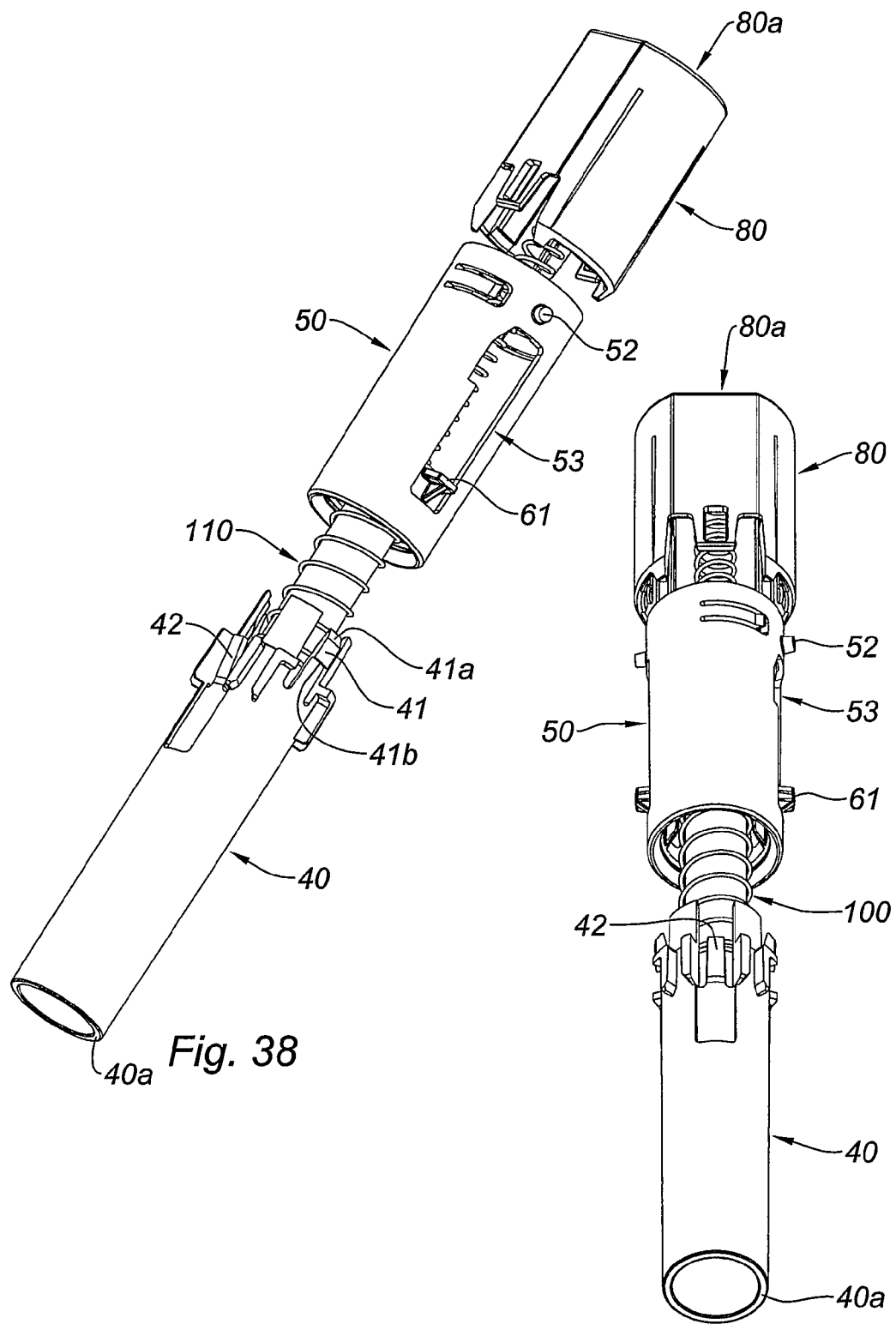

The invention and its advantages will appear more clearly in the light of the following description and the annexed drawing in which:

FIG. 1 is an exploded perspective view of a device according to the invention,

FIG. 2 is a cross section view of the device of FIG. 1 as provided to a user before use, FIG. 3 is a cross section view, taken after a rotation of 90° of the device of FIG. 2, FIGS. 4 and 5 are perspective views of the device of FIGS. 2 and 3 with the housing taken out, FIG. 6 is a partial side view of the housing and the sleeve of the device of FIGS. 1-5, FIG. 7 is a cross section view of the device of FIG. 1 after removal of the needle shield, FIG. 8 is a cross section view, taken after a rotation of 90° of the device of FIG. 7, FIG. 9 is a partial side view of the housing and the sleeve of the device of FIGS. 1-8 after removal of the needle shield, FIG. 10 is a partial perspective view of the housing and the sleeve of the device of FIGS. 1-9 after removal of the needle shield, FIG. 11 is a cross section view of the device of FIGS. 1-10 with the safety shield in its second position, FIG. 12 is a cross section view, taken after a rotation of 90° of the device of FIG. 11, FIG. 13 is a partial cross section view, taken after a slight rotation of the device of FIG. 11, FIGS. 14 and 15 are perspective views of the device of FIGS. 11-13 with the housing taken out, FIG. 16 is a partial side view of the housing and the sleeve of the device of FIGS. 1-15 when the safety shield is in its second position, FIG. 17 is a partial perspective view of the housing and the sleeve of the device of FIGS. 1-16 when the safety shield is in its second position, FIG. 18 is partial cross section view of the device of FIGS. 1-17 when the safety shield is in its third position, FIG. 19 is a cross section view, taken after a rotation of 90° of the device of FIG. 18, FIG. 20 is a partial cross section view, taken after a slight rotation of the device of FIG. 18, FIGS. 21 and 22 are perspective views of the device of FIGS. 18-20 with the housing taken out, FIG. 23 is a partial side view of the housing and the sleeve of the device of FIGS. 1-22 when the safety shield is in its third position, FIG. 24 is a partial cross section view of the device of FIGS. 1-23 after activation of the triggering means, FIG. 25 is a cross section view, taken after a rotation of 90° of the device of FIG. 24, FIG. 26 is a partial cross section view, taken after a slight rotation of the device of FIG. 24, FIGS. 27 and 28 are perspective views of the device of FIGS. 24-26 with the housing taken out, FIG. 29 is a partial cross section view of the device of FIGS. 1-27 at the end of injection, FIG. 30 is a cross section view, taken after a rotation of 90° of the device of FIG. 29, FIG. 31 is a partial cross section view, taken after a slight rotation of the device of FIG. 29, FIG. 32 is a partial cross section view of the device of FIGS. 1-27 at the end of injection in case of misuse of the device, FIG. 33 is a cross section view, taken after a rotation of 90° of the device of FIG. 32, FIG. 34 is a partial cross section view, taken after a slight rotation of the device of FIG. 32, FIG. 35 is a partial cross section view of the device of FIGS. 1-34 when the safety shield is in its fifth position, FIG. 36 is a cross section view, taken after a rotation of 90° of the device of FIG. 35, FIG. 37 is a partial cross section view, taken after a slight rotation of the device of FIG. 35, FIGS. 38 and 39 are perspective views of the device of FIGS. 35-37 with the housing taken out.

Referring now to the drawings, on FIG. 1 is shown an exploded view of a device 1 according to the invention for automatic injection of a product.

With reference to FIGS. 1 and 2, the device 1 comprises a container 20 having an open proximal end 20a and a substantially closed distal end, said container 20 being intended to receive a product 2 to be injected at an injection site 4 (see FIG. 11). The distal end of the container 20 is covered on FIG. 1 by a needle cap 21 in view of protecting a needle 3 provided at said distal end. As can be seen on FIG. 2, a piston 5 is lodged within said container 20, the distal movement of the piston 5 causing the product 2 to be expelled via the needle 3 at the time of injection. The device 1 has a longitudinal axis designated by the letter A on the figures.

The device 1 further comprises a housing 30 comprising a top body 30a and a bottom body 30b, said top and bottom bodies being coupled together after assembly of the device as shown on FIG. 2. As will appear hereinbelow, the housing 30 is intended to receive the container 20, said container 20 being movable relative to the housing 30 between an initial position (shown on FIGS. 7 and 8) to an insertion position (shown on FIGS. 24-25 and 29-30).

As appears more clearly from FIGS. 2 and 3, the top body 30a comprises an inner cylinder 32 provided with a radial rim 31 and with flexible legs 33. The inner cylinder 32 is also provided at its distal end with outer flexible tongues 34 extending in the proximal direction and having proximal ends 34a.

As shown on FIG. 3, the bottom body 30b is provided on its inner wall with radial projections 35.

In reference with FIGS. 1 and 6, the bottom body 30b is provided in its proximal region with a cam 36 and a window 37, the window 37 being distally spaced from the cam 36. The cam 36 is formed in its distal region of a first portion 36a and in its proximal region of a second portion 36b. The first portion 36a is inclined with respect to a longitudinal axis A of the device 1. The second portion 36b is longitudinal. The junction of the first and second portions (36a, 36b) of the cam 36 forms an elbow 36c.

The window 37 has a generally rectangular shape with a longitudinal axis parallel to the longitudinal axis of the device 1.

As better seen on FIG. 10, the bottom body 30b is provided on its inner wall with a longitudinal ridge 38.

The device 1 further comprises a safety shield 40: the safety shield 40 is received within the housing 30 and is movable with respect to said housing 30 as will appear later. The safety shield 40 is provided with proximal flexible legs 41. The proximal flexible legs 41 are provided with proximal inclined surfaces 41a and distal radial abutment surfaces 41b. The proximal region of the safety shield 40 is also provided with flexible tongues 42 extending in the outward direction. The safety shield 40 is further provided with an inner radial rim 43 (see FIG. 2).

The device 1 further comprises a sleeve 50. The sleeve 50 is provided at its proximal end with a projection 50a and at its distal end on its inner wall with a circumferential ridge 51 having a proximal abutment surface 51a (see FIG. 2). With reference to FIGS. 4 and 5, in its proximal region, the sleeve 50 is provided on its outer wall with a peg 52. The sleeve 50 is further provided with a first window 53 distally spaced from the peg 52 and having a substantially rectangular shape, the longitudinal axis of said first window 53 being parallel to the longitudinal axis A of the device 1. On one lateral wall of said first window 53 is located a recess 54 forming an abutment surface 54a. Tangentially spaced from the peg 52 is cut in the wall of the sleeve 50 a second window 55 in which a flexible tongue 56 is located, said flexible tongue 56 extending in the circumferential direction. The free end of said flexible tongue 56 is provided with a projection 57.

The device 1 further comprises a ring 60 received between the container 20 and the sleeve 50. The ring 60 comprises two radial stops 61 extending outwardly. The ring 60 is also provided with a skirt 62 extending distally.

The device 1 comprises a piston rod 70 and a push button 80. As shown on FIGS. 1-3, the piston rod 70 is provided at its distal end with an outer rim 71 and at its proximal end with an abutment rim 72. The push button 80 is provided with two distal legs 81 having distal ends 81b. The push button 80 is also provided with two inner legs 82 extending from the proximal end of the push button 80 and visible on FIG. 3.

At its distal end, the device 1 is further provided with a deshielder 90 intended to cover and to be coupled to the needle shield 21 before use.

The device 1 is further provided with two helical springs. A first helical spring 100 is received between the piston rod 70 and the push button 80. A second helical spring 110 is received between the container 20 and the safety shield 40.

With reference to FIGS. 2 to 6, the device 1 is in the state in which it is provided to the user. As can be seen on FIG. 6, in this position, the outer radial stop 61 of the ring 60 protrudes through both the window 37 of the bottom body 30b of the housing 30 and the first window 53 of the sleeve 50. In this position also, the peg 52 of the sleeve is located in the distal end of the first portion 36a of the cam 36 of the bottom body 30b of the housing 30.

The operation of the device 1 according to the invention will now be described in reference to FIGS. 2 to 39.

Once the user is ready to use the device 1 of the invention, he removes the deshielder 90 as shown on FIGS. 7 and 8. By removing the deshielder 90, he also removes the needle shield 21, and the device 1 is ready to be used. As appears from FIGS. 7 and 8, after removal of the deshielder 90, the distal end 40a of the safety shield 40 protrudes out of the bottom body 30b of the housing.

In this ready to use position, the container 20 is in its initial position. As can be seen from FIGS. 7 and 8, the tip 3a of the needle 3 extends neither beyond the distal end of the bottom body 30b of the housing 30 nor beyond the distal end 40a of the safety shield 40.

On FIGS. 7-9, the container 20 is also in a passive state: indeed, the removal of the deshielder 90 has allowed the ring 60 to move distally with respect to the sleeve 50 on a short distance until its outer radial stops 61 come in abutment against the abutment surface 54a of the window 53 of the sleeve 50, as shown on FIG. 9. In consequence, in this ready to use position, movement of said container 20 out of its initial position is prevented by means of the radial stops 61 of the ring 60 being in abutment on the abutment surface 54 of the first window 53 of the sleeve 50. The radial stops 61 of the ring 60 act as first retaining means for maintaining the container 20 in its passive state.

As shown on FIG. 7, in the ready to use position of the device 1, the distal end 81b of the distal leg 81 of the push button 80 faces the proximal end 34a of the outer flexible tongue 34 of the inner cylinder 32 of the top body 30a. In consequence, if a user wishes to push on the push button 80, the distal movement of the push button 80 is restricted by way of leg 81 coming in abutment against the proximal end 34a of the flexible tongue 34 and the triggering of the injection is not permitted. The device 1 is therefore in a passive state, and the distal end 81b of the distal leg 81 and the proximal end 34a of the flexible 34 act as second retaining means for maintaining the device 1 in a passive state.

Still with reference to FIGS. 7 and 8, the flexible legs 33 of the inner cylinder 32 of the top body 30a are engaged in the abutment rim 72 of the piston rod 70.

In the ready to use position, as shown on FIGS. 7 and 8, the proximal end of the first spring 100 bears on the radial rim 31 located on the inner cylinder 32 of top body 30a. The distal end of the first spring 100 bears on the outer rim 71 provided at the distal end of the piston rod 70. On these figures and in this ready to use position of the device 1, the first spring 100 is in a compressed condition. The radial rim 31 and the outer rim 71 on one hand, and the flexible legs 33 and the abutment rim 72 on the other hand, act as third retaining means for maintaining the first spring 100 in its compressed condition.

On these figures, the distal end of the second spring 110 bears on the proximal face of the inner radial rim 43 provided on the inner wall of the safety shield 40, and the proximal end of the second spring 110 bears on an inner abutment surface 63 located on the ring 60. In the before use position of the device 1, the spring 110 is in a partially compressed condition.

In the ready to use position shown on FIGS. 7 and 8, the safety shield 40 is coupled to sleeve 50 by means of the distal radial abutment surfaces 41b of the safety shield 40 being engaged on the proximal abutment surface 51a of the sleeve 50. The safety shield is in its first position.

In order to proceed with the injection, the container 20 must be placed in its active state. In this view, the user grabs the device 1 by the housing 30 formed of the top body 30a and the bottom body 30b and he applies the distal end of the device 1, namely the distal end 40a of the safety shield 40 on the site of injection 4 as shown on FIGS. 11 and 12. He then applies a distal force on the housing 30, for instance via the top body 30b, which causes the safety shield 40 to move in the proximal direction with respect to the housing 30. The sleeve 50 being coupled to the safety shield 40, the proximal movement of the safety shield 40 has the consequence to cause the movement of the peg 52 in the first portion 36a of the cam 36 of the bottom body 30b of the housing 30 as shown on FIGS. 16 and 17. The movement of the peg 52 in the inclined first portion 36a of the cam 36 causes the bottom body 30b of the housing 30 to rotate with respect to the sleeve 50. Since the ring 60 is engaged in the window 37 of the bottom body 30b via the radial stops 61 extending through said window 37, the ring 60 is coupled with the housing 30 and drawn with the bottom body 30b: in consequence, the ring 60 also rotates with respect to the sleeve 50: with this movement, the radial stops 61 of the ring 60 disengage from the abutment surface 54a of the first window 53 of the sleeve 50, as shown on FIGS. 14 and 16. This has the consequence of putting the container 20 in its active state, movement of said container 20 out of its initial position being no more prevented by the ring 60 being in abutment against the abutment surface 54c. Moreover, the safety shield 40 is now in its second position.

During the movement of the safety shield 40 from its first position to its second position as described above, the peg 52 and the first portion 36a of the cam 36 have acted as first guiding means for causing the translational and rotational movement of the sleeve 50. In an alternative embodiment of the device of the invention not shown, the peg is located on the housing and the cam is located on the sleeve.

The safety shield 40 has moved from its first position to its second position along a first distance D1 represented on FIG. 16. During this step, the sleeve 50 and its window 53 have moved coincident with the movement of the safety shield 40 on said first distance D1 so as to act as first deactivating means of the first retaining means, namely the outer radial stop 61 of the ring 60, and place the container 20 in its active state.

As shown on FIG. 17, during the rotation of the sleeve 50 with respect to the bottom body 30b of the housing 30, the flexible tongue 56 has also rotated with respect to the bottom body 30b and has overcome the longitudinal ridge 38 of the bottom body 30b. As appears on FIG. 17, the projection 57 of the flexible tongue 56 is now in abutment against the longitudinal ridge 38 therefore preventing any rotation back of the sleeve 50 with respect to the bottom body 30b of the housing 30. The function of said projection as such rotational stop will be explained later.

Due to the advantageous design of the present invention, a user need only use minimal force when applying the device 1 against his or her skin. To cause the safety shield 40 to rotate and move in the proximal direction and place the container 20 in the active state, the user applies the device 1 against his or her skin, and with a low force, causes the safety shield 40 to move in the proximal direction.

The container 20 is now in its active state. In this position, as shown on FIG. 13, the distal end 81b of the distal leg 81 of the push button 80 still faces the proximal end 34a of the flexible tongue 34 of the inner cylinder 32 of top body 30a of the housing 30. Distal movement of the push button 80 is therefore still restricted by the distal end 81b of distal leg 81 coming in abutment against the proximal end 34a of the flexible tongue 34 and the device 1 is therefore still in its passive state.

The user then continues to apply a small distal force on the housing 30 and in the same way as described above, since the safety shield 40 is still coupled to the sleeve 50 by means of flexible legs 41 being engaged in proximal abutment surface 51a of the sleeve, this causes the peg 52 to further move within the cam 36 of the bottom body 30b of the housing 30, this time within the second portion 36b of said cam 36, as shown on FIG. 17. This further movement of the peg 52 within the longitudinal second portion 36b of the cam 36 causes this time only proximal translation of the sleeve 50 with respect to the top body 30*a* of the housing 30. As shown on FIGS. 18 and 20, the projection 50*a* at the proximal end of the sleeve 50, by proximally translating with respect to the top body 30*a*, now pushes on the flexible tongue 34 of the top body 30*a*, thereby deflecting said flexible tongue 34 inwardly. As a consequence, the proximal end 34*a* of the flexible tongue 34 is driven away from the distal end 81*b* of the distal leg 81 of the push button 80. In consequence, the distal movement of the push button 80 is now allowed and by consequence, triggering of the injection is also now allowed. The device 1 is now in its active state. During this movement, once the peg 52 has reached the proximal end of the second portion 36*b* of the cam 36, as shown on FIG. 23, the safety shield 40 has moved to its third position.

In the step described above, the second portion 36*ab* of the cam 36 acts as second guiding means for causing the translational movement of the sleeve 50 with respect to the housing 30 when the safety shield 40 is moved from its second position to its third position. Since the direction of the second portion 36*b* of the cam is only longitudinal, the second portion 36*b* of the cam 36 prevents the rotation of the sleeve 50 with respect to the housing 30 as the safety shield is moved to its third position.

The safety shield 40 has moved from its second position to its third position along a second distance D2 represented on FIG. 23. During this step, the sleeve 50 and the projection 50*a* at its proximal end have moved coincident with the movement of the safety shield 40 on said second distance D2 so as to act as second deactivating means of the second retaining means, namely the proximal end 34*a* of the flexible tongue 34, and place the device 1 in its active state.

During the steps described above, the second spring 110 has been slightly compressed with respect to its initial condition.

The FIGS. 18-23 show the injection device 1 with both the container 20 and the device 1 in their respective active state.

The force needed by the user in order to apply the device 1 on the injection site and in order to move the safety shield 40 with respect to the housing 30 as described above is very low, in particular because part of the various deactivation of the retaining means is obtained by rotation of the intermediate sleeve 50 with respect to the housing 30. The device 1 is therefore very simple to use for the user.

With reference to FIGS. 24-28, the device 1 being now in its active state, the injection step as such may now be triggered by pushing distally on the pushing surface 80*a* of the push button 80.

With reference to FIG. 25, by pushing distally on the push button 80, the inner legs 82 of the push button 80 deflect the flexible legs 33 of the top body 30*a* and therefore free the spring 100 which extends in the distal direction in view of returning to an uncompressed condition. By extending, the spring 100 draws with him the container 20 which, because it is in its active state, is allowed to move distally, thereby causing the penetration of the needle 3 in the injection site 4. As shown on FIGS. 24, 25 and 27 and 28, the tip 3*a* of the needle 3 now extends beyond the distal end 40*a* of the safety shield 40 and the proper injection of the product 2 contained in the container 20 can take place.

During the insertion step just described, the second spring 110 has been compressed, as shown on FIGS. 24 to 26, due to the distal movement of the container 20. During this movement, the ring 60 has been drawn by the container 20 and has moved distally with respect to the sleeve 50 until its distal skirt 62 has become inserted between the proximal flexible legs 41 of the safety shield 40 and the sleeve 50, thereby deflecting inwardly said proximal flexible legs 41 and disengaging said proximal flexible legs 41 from the proximal abutment surface 51*a* of the circumferential ridge 51 of the sleeve 50, as shown on FIGS. 24 and 26.

In the third position of the safety shield 40, the proximal flexible legs 41 engaged in the proximal abutment surface 51*a* of the circumferential ridge 51 of the sleeve 50 acted as arresting means for maintaining said safety shield 40 in its third position.

The distal skirt 62 of the ring, by deflecting said flexible legs 41, acts as third deactivating means for deactivating the arresting means. The disengagement of the proximal flexible legs 41 from the circumferential ridge 51 causes the safety shield 40 to be in a fourth position, in which the tip 3*a* of the needle 3 extends beyond the distal end 40*a* of the safety shield 40 and in which distal movement of the safety shield 40 with respect to the container 20 is allowed upon release of distal pressure exerted on the housing 30. In this fourth position of the safety shield 40, said safety shield 40 is no more coupled to the sleeve 50.

A case of misuse by the user is the following one: after having done the necessary as described above in order to put both the container 20 and the device 1 in their respective active state, the user may begin to push distally on the push button 80 and almost simultaneously he withdraws the device 1 from the injection site, for example on a distance of 1 mm. Usually, the user will not even notice he has withdrawn the device from the injection and he will carry on applying a force on the push button. In devices of the prior art, in such a case, the push button is allowed to move distally, the spring is freed as described above and the injection is completed although not at the right insertion depth. In some devices of prior art comprising a ring such as the one described above, such ring may then never reach the flexible legs 41 and the safety shield 40 is not allowed to extend at the end of injection, rendering the device very dangerous.

The device 1 of the present invention shown on FIGS. 1-39 remedies this problem. When the container 20 and the device 1 of the invention are in their respective active state as shown on FIGS. 18 to 20, if the user begins to push distally on the push button 80, and then withdraws the device 1 from the injection site 4 for about 1 mm for example, then the sleeve 50 is only allowed to translate back on the very short distance defined by the second portion 36*b* of the cam 36, that is on distance D2, but it is not allowed to rotate back because of the projection 57 of the flexible tongue 56 of the sleeve 50 being in abutment on the longitudinal ridge 38 of the bottom body 30*b* of the housing 30 (se FIG. 17). In consequence, the peg 52 is stuck on the elbow 36*c* of the cam 36 and the sleeve 50 can not rotate back. In such a configuration, as can be easily understood from FIG. 16, the ring 60 remains disengaged from the abutment surface 54*a* of the first window 53 of the sleeve 50. In consequence, because the ring 60 remains disengaged from the abutment surface 54*a*, when the user continues applying a distal force on the push button 80, the container 20 is still in its active state and is allowed to move distally: the penetration of the injection site 4 by the needle 3 takes place and the injection can be completed in a correct way, although the user has misused the device 1 in the first place.

In correct use of the device 1, with reference to FIGS. 29 to 31, the injection is completed by virtue of first spring 100 acting as a biasing means on the piston rod 70 and causing the distal movement of the piston rod 70 which reaches the piston 5 and pushes said piston 5 distally, thereby causing the product to be expelled via the needle 3. On FIGS. 29 to 31, the first spring 100 is in its expanded state, the piston 5 has reached the distal end of the container 20 and all the product 2 has been expelled.

Moreover, in case of misuse as described above, as can be seen on FIGS. 32-34, since the sleeve 50 has moved back on the distance D2 corresponding to the length of the second portion 36*b* of the cam 36, the ring 60 does not reach the bottom end of the sleeve 50, as it was the case in normal use shown on FIG. 24: yet said ring 60 has moved distally on a sufficient distance with respect to the sleeve 50 in order to deflect the proximal flexible legs 41 of the safety shield 40, as shown on FIGS. 32 and 34 so as to disengage them from the proximal surface abutment 51*a* of circumferential ridge 51 of the sleeve 50 and therefore put the safety shield 40 in its fourth position, in which said safety shield 40 is no more coupled to said sleeve 50 and in which distal movement of said safety shield 40 is allowed upon release of distal pressure exerted on said housing 30.

In consequence, at the end of the injection, because of the disengagement of the flexible legs 41 from the ridge 51, the withdrawal of the device 1 from the injection site causes the distal movement of the safety shield 40 drawn by the second spring 110 tending to come back to an extended condition. As shown on FIGS. 35-39, the safety shield 40 has moved from its fourth position to its fifth position and it now covers the needle 3 and the injection device 1 can be safely handed.

As shown on FIG. 36, the safety shield 40 is now locked in its fifth position by means of flexible tongues 42 being blocked against the radial projections 35 of the bottom body 30*b* in the proximal direction. Indeed, during the distal movement of the safety shield 40 from its fourth position to its fifth position, the flexible tongues 42, due to the fact that they extend in the outward direction, have been able to overcome the radial projections 35.

The radial projections 35 now act as a stop and prevent the proximal movement of the safety shield 40 with respect to the container 20, once said safety shield 40 is in its fifth position. The safety shield 40 is therefore prevented to move back to a retracted position and the device 1 is totally safe and can disposed of.

The device of the invention only requires a low force to be applied by the user on the housing at the time of injection. For example the needed force may be inferior to 5 Newton. Moreover, the device of the invention reduces the risk of potential mis-use by the user. In particular, in case the user mis-uses the device of the invention, then the product is not lost and the injection may be correctly and safely completed in the end.

The invention claimed is:

1. A device (1) for automatic injection of a product (2) into an injection site (4), said device being in one of a passive and active state, triggering of injection being prevented when said device (1) is in its passive state and permitted when said device (1) is in its active state, said device having:
  a housing (30, 30*a*, 30*b*) capable of receiving a container, the container being movable relative to the housing between an initial position and an insertion position distally spaced from the initial position, the container being in one of a passive state and an active state, movement of the container out of its initial position being prevented when the container is in its passive state, and being permitted when the container is in its active state, and
  a safety shield (40) coupled with the housing (30) and being movable with respect to the housing along a movement path having a predetermined length, the safety shield being movable between a first position and a second position a first distance that is less than the predetermined length, and between the second position and a third position a second distance that is less than the predetermined length,
  first retaining means (60, 61, 54*a*) for maintaining the container (20) in its passive state,
  second retaining means (34*a*, 81*b*) for maintaining said device (1) in its passive state,
  said device (1) being characterized in that it further comprises:
  first deactivating means (50, 53) movable coincident with movement of the safety shield (40) the first distance to cooperate with first retaining means (61, 54*a*) so as to place the container (20) in the active state, and
  second deactivating means (50, 50*a*) movable coincident with movement of the safety shield (40) the second distance to cooperate with second retaining means (34*a*, 81*b*) so as to place the device (1) in its active state,
  wherein part of the first and second deactivating means are formed on a sleeve (50) coupled to the safety shield (40) and being received within said housing (30), the sleeve (50) moving in rotation and in translation with respect to the housing (30) when the safety shield (40) moves from its first position to its second position, the sleeve (50) moving in translation with respect to the housing (30) when the safety shield (40) moves from its second position to its third position.

2. Device (1) according to claim 1, wherein
  said first retaining means comprises a ring (60, 61) coupled with the housing (30), the ring (60) comprising at least one outer radial stop (61),
  the first deactivating means comprises a window (53) defined in the sleeve (50) and having an abutment surface (54*a*),
  the outer radial stop (61) being engageable with the abutment surface (54*a*) when the safety shield (40) is in its first position, and being disengageable from the abutment surface (54*a*) when the safety shield (40) is moved from its first position to its second position.

3. Device (1) according to claim 1, wherein
  the second retaining means comprises a radially deflectable leg (34) coupled to the housing (30),
  the second deactivating means comprises a projection (50*a*), defined at a proximal end of said sleeve (50), the projection (50*a*) being capable of deflecting the radially deflectable leg (34) from a rest position, in which the radially deflectable leg (34) maintains the device (1) in its passive state, to a deflected position, in which the device is in its active state, deflection of the radially deflectable leg (34) from its rest position to its deflected position being caused by movement of the safety shield (40) from its second position to its third position.

4. Device (1) according to claim 1, wherein it further comprises first guiding means (36, 36*a*, 52) for causing the translational and rotational movement of the sleeve (50) when the safety shield (40) is moved from its first position to its second position, and second guiding means (36, 36*b*, 52) for causing the translational movement of the sleeve (50) with respect to the housing (30) when the safety shield (40) is moved from its second position to its third position, the second guiding means (36, 36*b*, 52) preventing the rotation of the sleeve (50) with respect to the housing (30) as the safety shield (40) is moved to its third position.

5. Device (1) according to claim 4, wherein the first guiding means (36*a*) defines the first distance, and wherein the second guiding means (36*b*) defines the second distance.

6. Device (1) according to claim 4, wherein said first guiding means includes a peg (52) located on the sleeve (50) or on the housing (30) and a first portion (36a) of a cam (36) located respectively on the housing (30) or on the sleeve (50) and in which the peg (52) is engaged so as to be able to move slidingly within the cam (36), the first portion (36a) of the cam (36) being inclined with respect to the longitudinal axis A of the device (1), movement of the peg (52 within the first portion (36a) of the cam (36) causing translational and rotational movement of the sleeve (50) when the safety shield (40) is moved from its first position to its second position.

7. Device (1) according to claim 6, wherein the second guiding means include a second portion (36b) of the cam (36), the second portion (36b) being longitudinal, the junction of the first and said second portions (36a, 36b) of the cam (36) forming an elbow (36c), the movement of the peg (52) within the second portion (36b) of the cam (36) causing translational movement of the sleeve (50) when the safety shield (40) is moved from its second position to its third position.

8. Device (1) according to claim 1, wherein said device (1) further comprises:
first biasing means (100) coupled to the housing (30) for biasing the container (20) toward the insertion position, the first biasing means (100) being in one of a compressed condition, in which the container (20) is in its initial position, and an extended condition, in which the container (20) is in its insertion position, and
third retaining means (31, 33, 71, 72) for maintaining the first biasing means (100) in its compressed condition,
triggering means (80) being user activatable for releasing the third retaining means (33, 72), once the device (1) is in its active state.

9. Device (1) according to claim 8, wherein it further comprises first guiding means (36, 36a, 52) for causing the translational and rotational movement of the sleeve (50) when the safety shield (40) is moved from its first position to its second position, and second guiding means (36, 36b, 52) for causing the translational movement of the sleeve (50) with respect to the housing (30) when the safety shield (40) is moved from its second position to its third position, the second guiding means (36, 36b, 52) preventing the rotation of the sleeve (50) with respect to the housing (30) as the safety shield (40) is moved to its third position.

10. Device (1) according to claim 9, wherein said first guiding means includes a peg (52) located on the sleeve (50) or on the housing (30) and a first portion (36a) of a cam (36) located respectively on the housing (30) or on the sleeve (50) and in which the peg (52) is engaged so as to be able to move slidingly within the cam (36), the first portion (36a) of the cam (36) being inclined with respect to the longitudinal axis A of the device (1), movement of the peg (52) within the first portion (36a) of the cam (36) causing translational and rotational movement of the sleeve (50) when the safety shield (40) is moved from its first position to its second position.

11. Device (1) according to claim 10, wherein the second guiding means include a second portion (36b) of the cam (36), the second portion (36b) being longitudinal, the junction of the first and said second portions (36a, 36b) of the cam (36) forming an elbow (36c), the movement of the peg (52) within the second portion (36b) of the cam (36) causing translational movement of the sleeve (50) when the safety shield (40) is moved from its second position to its third position.

12. Device (1) according to claim 11, wherein it comprises return means (110) for biasing the safety shield (40) from its third position to its second position after activation of the triggering means (80) but before the container (20) reaches its insertion position, the second guiding means (36b, 52) causing the sleeve (50) to move translationally in the distal direction with respect to the housing (30) until the peg (52) comes in abutment with the elbow (56c) formed at the junction between the first portion (36a) and second portion (36b) of the cam (36).

13. Device (1) according to claim 12, wherein said return means comprise a spring (110) in a compressed condition when the safety shield (40) is in its third position.

14. Device (1) according to claim 13, wherein said device (1) further comprises locking means (38, 56, 57) for preventing the sleeve (50) to rotate back with respect to the housing (30) under the effect of said return means (110), the locking means comprising a rotational stop (57) located on the sleeve (50) or on the housing (30), the rotational stop (57) being engaged in abutment against a longitudinal ridge (38) located on the housing (30) or respectively on the sleeve (50), thereby preventing the rotation of the sleeve (50) with respect to the housing (50).

15. Device (1) according to claim 14, wherein:
the safety shield (40) being movable with respect to the container (20) from its third position, in which the tip (3a) of the needle (3) does not extend beyond a distal end (40a) of the safety shield (40), to a fourth position, in which the tip (3a) of the needle (3) extends beyond a distal end (40a) of the safety shield (40), and to a fifth position, in which the tip (3a) of the needle (3) does not extend beyond a distal end (40a) of the safety shield (40), movement of said safety shield (40) from its fourth position to its fifth position being caused by release of a distal pressure exerted on said housing (40),
said device (1) further comprises
arresting means (41, 51, 51a) for maintaining the safety shield (40) in its third position, in which the release of the distal pressure exerted on said housing (30) does not cause the safety shield (40) to move to its fifth position,
third deactivating means (60, 62)) designed for deactivating the arresting means when the safety shield (40) is in its fourth position
second biasing means (110) coupled to the safety shield (40) for biasing the safety shield (40) from its fourth position to its fifth position when distal pressure exerted on the housing (30) is released.

16. Device (1) according to claim 15, wherein the arresting means comprises a flexible leg (41) located on the safety shield (40), the flexible leg (41) being engaged on an abutment surface (51a) located on the sleeve (50) so as to maintain the sleeve (50) coupled to the safety shield (40) when the safety shield (40) is in its third position.

17. Device (1) according to claim 16, wherein the ring (60) being coupled to the container (20),
the third deactivating means comprises a distal skirt (62) located on the ring (60), the distal skirt (62) cooperating with the flexible leg (41) located on the safety shield (40) so as to deflect the flexible leg (41), when the container (20) moves from its initial position to its insertion position, thereby causing the safety shield to be in its fourth position.

* * * * *

UNITED STATES PATENT AND TRADEMARK OFFICE
CERTIFICATE OF CORRECTION

PATENT NO. : 8,357,125 B2  Page 1 of 1
APPLICATION NO. : 12/679989
DATED : January 22, 2013
INVENTOR(S) : Grunhut et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 279 days.

Signed and Sealed this
First Day of September, 2015

Michelle K. Lee
*Director of the United States Patent and Trademark Office*